US008420322B2

(12) United States Patent
Levin et al.

(10) Patent No.: US 8,420,322 B2
(45) Date of Patent: Apr. 16, 2013

(54) ISOLATED NUCLEOTIDE SEQUENCES RESPONSIBLE FOR THE TOMATO HIGH PIGMENT-1 MUTANT PHENOTYPE (HP-1) AND USES THEREOF

(75) Inventors: Ilan Levin, Mazkeret Batia (IL); Michal Lieberman, Rishon le-Zion (IL); Orit Amir Segev, Holon (IL); Nehama Gilboa, Rishon le-Zion (IL); Avraham Lalazar, Makeret Batia (IL)

(73) Assignee: The Volcani Center—The State of Israel Ministry of Agriculture, Agricultural Research Organization, Bet Dagan (IL)

( * ) Notice: Subject to any disclaimer, the term of this patent is extended or adjusted under 35 U.S.C. 154(b) by 1018 days.

(21) Appl. No.: 10/576,730

(22) PCT Filed: Oct. 20, 2004

(86) PCT No.: PCT/IL2004/000956
§ 371 (c)(1),
(2), (4) Date: May 4, 2009

(87) PCT Pub. No.: WO2005/037987
PCT Pub. Date: Apr. 28, 2005

(65) Prior Publication Data
US 2009/0217405 A1    Aug. 27, 2009

Related U.S. Application Data

(60) Provisional application No. 60/512,774, filed on Oct. 21, 2003.

(51) Int. Cl.
*C12Q 1/68*     (2006.01)
*C12N 15/82*    (2006.01)

(52) U.S. Cl.
USPC .................. 435/6.12; 435/91.1; 536/23.2

(58) Field of Classification Search .................. None
See application file for complete search history.

(56) References Cited

U.S. PATENT DOCUMENTS 6,429,299 B1 *  8/2002  Bowler et al. ................ 536/23.1

FOREIGN PATENT DOCUMENTS
WO    03/057917 A2    7/2003

OTHER PUBLICATIONS

Yongsheng Liu et al., Manipulation of Light Signal Transduction as a Means of Modifying Fruit Nutritional Quality in Tomato, Jun. 2004, PNAS 101(26) 9897-9902.*
Janny Peters et al., The Expression of Light-Regulated Genes in the High-Pigment-1 Mutant of Tomato, 1998, 117 797-807.*
Yen et al. The tomato high-pigment (hp) locus maps to chromosome 2 and influences the plastome copy and fruit quanlity, 1997, Theo. Appl. Genet. 95:1069-1079.*
Ishibashi T, Kimura S, Yamamoto T, Furukawa T, Takata K, Uchiyama Y, Hashimoto J, Sakaguchi K (2003) Rice UV-damaged DNA binding protein homologues are most abundant in proliferating tissues. Gene 308: 79-87.
Schroeder DF, Gahrtz M, Maxwell BB, Cook RK, Kan JM, Alonso JM, Ecker JR, Chory J (2002) De-etiolated 1 and damaged DNA binding protein 1 interact to regulate Arabidopsis photomorphogenesis. Curr Biol. 12: 1462-1472.
GenBank Accession AW617366 (Mar. 24, 2000 uploaded) [onine] (http://www.ncbi.nlm.nih.gov/sviewer/viewer.fcgi?val=7323524&sat=EST&satkey=4051974).
GenBank Accession NM_116781 (Sep. 16, 2003 updated) [online] (http://www.ncbi.nlm.nih.gov/sviewer/viewer.fcgi?val=30680092&sat=OLD03&satkey=5220679).
GenBank Accession AB037144 (Apr. 23, 2003 updated) [online] (http://www.ncbi.nlm.nih.gov/sviewer/viewer.fcgi?val=12082086&sat=OLD04&satkey-10267903).

* cited by examiner

*Primary Examiner* — Brent T Page
*Assistant Examiner* — Lee A Visone
(74) *Attorney, Agent, or Firm* — Browdy and Neimark, PLLC

(57) ABSTRACT

The present invention provides isolated nucleotide sequences responsible for the tomato high pigment 1 (hp-1) and high pigment $1^w$ (hp-$1^w$) phenotypes, wherein said sequences comprises an altered tomato DDB1 gene sequence or fragment thereof, wherein said the alteration in said altered sequence or fragment comprises an A-to-T transversion at nucleotide 931 of said DDB1 gene sequence in the case of hp-1 and a G-to-A transition at nucleotide 2392 of said DDB1 gene sequence in the case of hp-$1^w$.

5 Claims, 7 Drawing Sheets

Fig. 1.

CTCATGAGAAGGAGAAGTGCGTCAGCATTTTCTAGACTGTCATTTCTACTTTAGCTGAGT
TGCTGGGAATGAAATCTTCTCTTGTACCCCTGCCTGGTTGCTGGAATAAAAATGTTTAAT
TTGGATTGTTAACCTGTTTTCCAGAGTTACCGGACTCAAAATTGAGCTACTGGGGGAAAC
TTCTATTGCATCAACCATATCATACCTAGACA/TATGCTTTTGTCTTCATTGGCTCAAG
CTACGGAGATTCACAGGTACTTTTAACTGTTGAGTGCATCTTGGTGCAATAAGTTGGTTT
TTAGAGCTGCCTTATTGTATTTTCCATACAGTAGCCTTTCATTCATTTGGAACATTGAGG
TTTTAAATTTCAGTTGCCTATTTCTGGTGGTGCTTCATATTTCACAGTTCCACTAATATT
TTTGAATTCACGTTTAGCTTGTAAAGCTCAATCTCCAGCCTGACACCAAA

Fig. 3
a. *hp-1/hp-1*
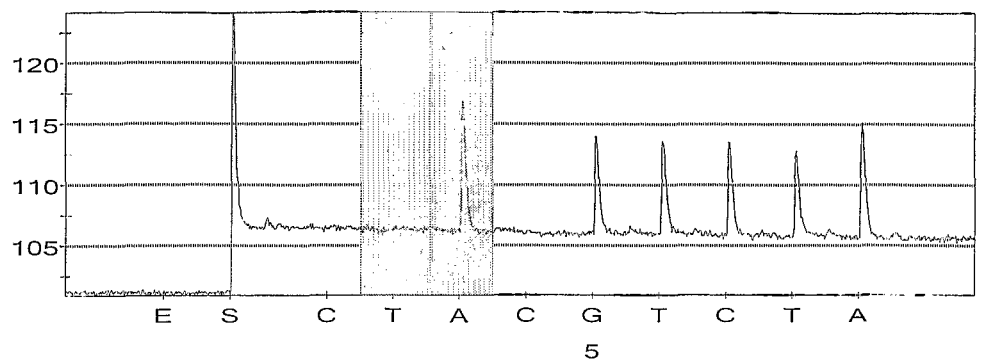
b. +/+
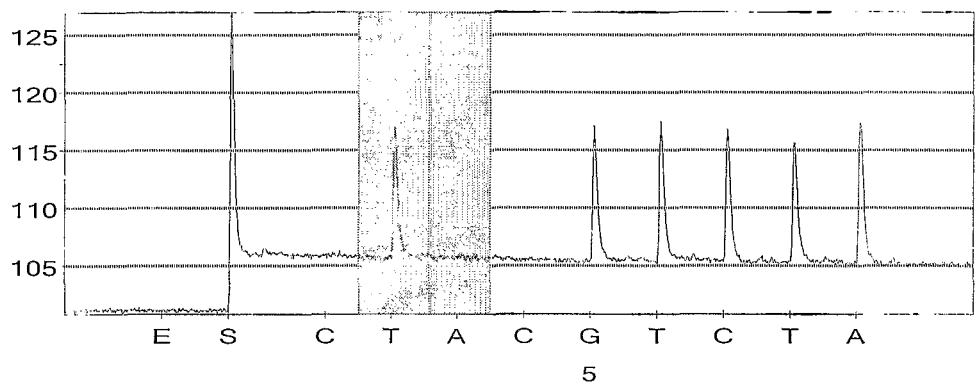
c. *hp-1/+*
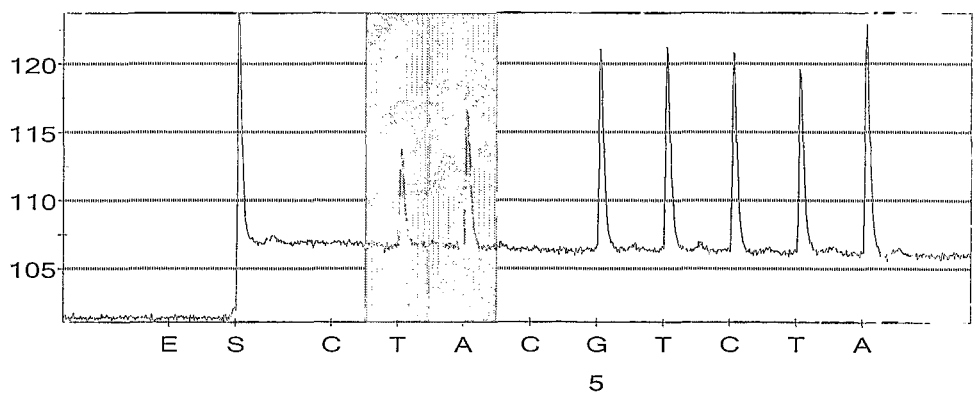

Fig. 5A

```
   1 ATGAGTGTATGAACTACGTGGTTACGGCTCACAAACCAACAAATGTTACACATTCCTGTGTTGGCAATTTCACCGTCC
  81 TCAAGAGCTCAATCTTATCATTGCGAAATGTACTCGAATGTGAGATTCATTTACTTACTCCCAAGGTTTACAGCCTATGT
 161 TAGATGTGCCAATATATGGAGGATCGCGACACTTGAGCTTTTTCGTCCTCACGGTGAAACACAAGATCTTCTCTTCATC
 241 GCAACAGAGCGATATAAATTCTGTGTCCTTCAATGGATACTGAGGCATCTGAAGTTATCACAAGAGCAATGGGAGATGT
 321 GTCAGACCGAATAGGCCCGTCCCACAGATAAATGGTCAGATTGGTATAATTGATCAGATTGCAGATTGATCGGGCTACATC
 401 TTTATGATGGACTATTTAAGGTTATTCCATTTGATAACAAAGGCCAACTGAAGGAAGCTTTTAACATCAGGATAACAAGGATGC
 481 CTTCAAGTTTTAGATATTAAATTCTTGTATGGTTGCCCAAAGCCTACAATTGTGTTCTATATCAGGATAACAAGATGA
 561 CCGGCATGTCAAAACATATGAGGTGTCCTTGAAAGACAAAGATTTTATTGAAGGGCCATGGCTCAAAATAATCTTGATA
 641 ATGGAGCTTCTCTTTGCTAATACCAGTACCTCCACCACTTGTGTGTATTGATTATTGGAGAAGAAACCATCGTTATTGC
 721 AGCGCTTCAGCTTTTAAGGCTATCCCAATTAGACCTTCTATCACAGAGCATATGGGCGGTTGATGCTGATGGTTCTCG
 801 ATATTGCTTGGGGATCATAATGGGCTTCTTCACCTACTTGTAATCACTCATGACGAAGGAGAAAGTTACCGACTCAAAA
 881 TTGAGCTACTGGGGAAACTTCTATTGCATCAACCATATCATCATACCTAGACAATGCTTTTGTCTTCATTGGCTCAAGCTAC
 961 GGAGATTCACACAGCTTGTAAAGCTTGTAAAGCTTGCTAGTGGAAGTTCTCTATGTGAAGTTCTAGAGAGATATGTCAA
1041 TTTTAGGACCTATTGTGACTTCTCGTTGTTGATCTGAAATGGCAAGTCAAGTCAGTTGTGAACTTGCTCTGGAGCCT
1121 ATAAGGATGGATCACTTCGTATTGTTCGACTGCTCCATATGACACATTGACACATTCTCAAGTCCAGACCTTGTTTTGTC
1201 GGAATGTGCTTGGTCTCTTAGATCTGCTAGATGATCCATATGAAGAACTGAGAAACTGAGGGAGGCTTCAATTCTCAAGTCCAGACCTTGTTTTGTC
1281 TTTGGCTATGAACCTTGAGGATGAGCTGTTCAGTTGTTCTTGTTAGATTGGTCAGTTCTACACCTCTAGAGATCTGAAA
1361 ATGATGCTGTATACAACCAGCTCGGCTACTCGGTCAATGTTGCAACTGCTAATGCCACTCAGGTACTATTGGCTACTGGGGG
1441 AACGAGTGGTTTGCCCCAGTCGGCTACTCGGTCAATGGTGTGATGGGGTGTTGAATGAAGTAAAATATGCCAAGTTGGATTATGATATCTCGT
1521 TGGCCATCTGGTATACCTAGAGAATTGGTGATGGGGTGTGATGGGGTGTTGAATGAAGTAACAGTAACATTGCAGCAGTTGGAATGTGGACAGACATAAGTGTC
1601 GCCTGGACATAAATCCAATTGGTGAAAATCCGAACTACAGTAACATTGCAGCAGTTGGAATGTGGACAGACATAAGTGTC
1681 AGGATATATTCACTTCCTGAAGGGATATCTTATCTACTACTGAATCTCATTACAAAGGAACACAGCTAGGAGGGAGATAATTCCTCGTCTTCTGAT
1761 GTGTTCCTTCGAAGGGATATCTTATCTACTACTGTGCTTTGGGAGATGCCATCTCTTGAATTTTGTATTGAGCATGAGTA
1841 CTGGTGAGCTGACAGATAGAGAAAAAAGTTTCTCTTGGGACACAGCCCATAACACTTCGTACATTCTCATCTAAAGATACT
```

Fig. 5B

```
1921 ACACATGTCTTTGCTGCCTCCGATAGGCCAACACAGTTATTTACAGCAGTAACAAGAGAAGCTGCTTTATAGCAATGTAAATCT
2001 AAAAGAAGTTAGTCATATGTGCCCATTCAATGTGCAGCTTTTCCAGACAGCCTTGCAATCGCTAAAGAAGGTGAGTTAA
2081 CAATTGGCACTATTGATGAAATTCAAAAGCTTCACATTCGTTCATATCCCCCTTGGGAGCATGCACGTCGCATCAGCCAT
2161 CAAGAGCAGACCCGGACATTTGCTCTATGCAGTGTGAAGTATACTCAGTCAAATGCAGATGATCCTGAAATGCATTTGT
2241 CCGGCCTGTTGGATGATCAGACATTTGAGTTCATATCAACATATCCCCTTGACCAATTTGAATATGGCTGTTCCATACTAA
2321 GCTGCTCCTTTTCTGATGATAGTAAATGTGTATTATTGCATTGGAACTGCATATGTGATGCCAGAGGAAAATGAACCTACT
2401 AAGGGCCGAATTTTAGTTTTTTATAGTTGAAGATGGAAAGCTCCAGCTAATTGCTGAGAAGGAAACTAAGGGAGCTGTCTA
2481 CTCTCTAAATGCCTTGCAATGGGAAACTGCTTGCTGCAATCAATCAGAAGATTCAATTGTACAAGTGGGCTTCGCGTGAGG
2561 ATGGTGGCAGCCGAGAATTGCAGACAGAATGTGGACACCATGGTCATTTCTCTGCTGATTTTCAAGCATGAAGAGGGTGCTATAGAGGAGCGAGC
2641 TTCATTGTTGTTGGTGATTGATGAAATCCATTTCTCTGCTGTTGAGATTCTCGATGATGACATTTATCTTGGTGCTGAGAATAACTTCA
2721 CAGAGACTATAATGCAAATTGGATGTCAGCTTGTTGAGGTGCTACAGATGGAGGTGCACTTGGTCATGCGACTACCAGATTCAGATGTTGGGCAGATACCCAC
2801 ACCTTTTCACGGTCAGGAATTGTTAATAGTTTAGACATGGTTCACTTGTCATGCGACTACCAGATTCAGATGTTGGGCAGATACCCAC
2881 CTTGGCGAATTTGTTGGCACAGTGAATGGTGTTATAGGGGTGTGGGAGATTGAATCATTCCTAGATCATTGGAGAAGC
2961 TGTCATATTTGGCACAGTGAATGGTGTTATAGGGGTGTGGGAGGTCATGAGCCATGAGCAGTGGAGGTCGTTTACAATGAGAAG
3041 TGCAGACAAACTTACGGAAAGTGATAAAAGTGCTAAAACTTTCTTGATGGAGAATTGAATCATTCCTAGATCTTAGCAGGAATAGGATGGAAGA
3121 AAAACAGTAGATGCTAAAAACTTTCTTGATGGAGAACTAATGAAGAGAGTTGACAAGGTTGCATTAG
3201 GATTTCAAAGGCTATGTCAGTTCCAGTTGAGGAACTAATGAAGAGAGTTGACAAGGTTGCATTAG
```

Fig. 6

```
   1 MSVWNYVVTAHKPTNVTHSCVGNFTGPQELNLIIAKCTRIEIHLLTPQGLQPMLDVPIYGRIATLELFRPHGETQDLLFI
  81 ATERYKFCVLQWDTEASEVITRAMGDVSDRIGRPTDNGQIGIIDPDCRLIGLHLYDGLFKVIPFDNKGQLKEAFNIRLEE
 161 LQVLDIKFLYGCPKPTIVVLYQDNKDARHVKTYEVSLKDKDFIEGPWAQNNLDNGASLLIPVPPLCGVLIIGEETIVYC
 241 SASAFKAIPIRPSITRAYGRVDADGSRYLLGDHNGLLHLLVITHEKEKVTGLKIELLGETSIASTISYLDNAFVEIGSSY
 321 GDSQLVKLNLQPDTKGSYVEVLERYVNLGPIVDFCVVDLERQGQGQVVTCSGAYKDGSLRIVRNGIGINEQASVELQGIK
 401 GMWSLRSATDDPYDTFLVVSFISETRVLAMNLEDELEETEIEGFNSQVQTLFCHDAVYNQLVQVTSNSVRLVSSTSRDLK
 481 NEWFAPVGYSVNVATANATQVLLATGGGHLVYLEIGDGVLNEVKYAKLDYDISCLDINPIGENPNYSNIAAVGMWTDISV
 561 RIYSLPDLNLITKEQLGGEIIPRSVLMCSFEGISYLLCALGDGHLLNFVLSMSTGELTDRKKVSLGTQPITLRTFSSKDT
 641 THVFAASDRPTVIYSSNKKLLYSNVNLKEVSHMCPFNVAAFPDSLAIAKEGELTIGTIDEIQKLHIRSIPLGEHARRISH
 721 QEQTRTFALCSVKYTQSNADDPEMHFVRLLDDQTFEFISTYPLDQFEYGCSILSCSFSDDSNVYYCIGTAYVMPEENEPT
 801 KGRILVFIVEDGKLQLIAEKETKGAVYSLNAFNGKLLAAINQKIQLYKWASREDGGSRELQTECGHHGHILALYVQTRGD
 881 FIVVGDLMKSISLLIFKHEEGAIEERARDYNANWMSAVEILDDIYLGAENNFNLFTVRKNSEGATDEERSRLEVVGEYH
 961 LGEFVNRFRHGSLVMRLPDSDVGQIPTVIFGTVNGVIGVIASLPHDQYLFLEKLQTNLRKVIKGVGGLSHEQWRSFYNEK
1041 KTVDAKNFLDGDLIESFLDLSRNRMEEISKAMSVPVEELMKRVEELTRLH
```

```
                       SEQUENCE LISTING

<160> NUMBER OF SEQ ID NOS: 37

<210> SEQ ID NO 1
<211> LENGTH: 3273
<212> TYPE: DNA
<213> ORGANISM: Lycopersicon esculentum

<400> SEQUENCE: 1
atgagtgtat ggaactacgt ggttacggct cacaaaccaa caaatgttac acattcctgt      60
gttggcaatt tcaccggtcc tcaagagctc aatcttatca ttgcgaaatg tactcgaatc     120
gagattcatt tacttactcc ccaaggttta cagcctatgt tagatgtgcc aatatatggg     180
aggatcgcga cacttgagct ttttcgtcct cacggtgaaa cacaagatct tctcttcatc     240
gcaacagagc gatataaatt ctgtgtcctt caatgggata ctgaggcatc tgaagttatc     300
acaagagcaa tgggagatgt gtcagaccga ataggccgtc ccacagataa tggtcagatt     360
ggtataattg atccagattg cagattgatc gggctacatc tttatgatgg actatttaag     420
gttattccat ttgataacaa aggccaactg aaggaagctt taacatcag gctcgaggag     480 cttcaagttt tagatattaa attcttgtat ggttgcccaa agcctacaat tgttgttcta     540
tatcaggata acaaggatgc ccggcatgtc aaaacatatg aggtgtcctt gaaagacaaa     600
gattttattg aagggccatg ggctcaaaat aatcttgata atggagcttc tttgctaata     660
```

```
ccagtacctc caccactgtg tggtgtattg attattggag aagaaaccat cgtttattgc    720
agcgcttcag cttttaaggc tatcccaatt agaccttcta tcacaagagc atatgggcgg    780
gttgatgctg atggttctcg atatttgctt ggggatcata atgggcttct tcacctactt    840
gtaatcactc atgagaagga gaaagttacc ggactcaaaa ttgagctact ggggaaact    900
tctattgcat caaccatatc atacctagac tatgcttttg tcttcattgg ctcaagctac    960
ggagattcac agcttgtaaa gctcaatctc cagcctgaca ccaaaggttc ttatgtggaa   1020
gttctagaga gatatgtcaa tttaggacct attgtggact tctgtgttgt tgatctggaa   1080
aggcaaggtc aaggtcaggt tgtaacttgc tctggagcct ataaggatgg atcacttcgt   1140
attgttcgaa atggaattgg cataaatgaa caggcgtctg tggaactaca agggatcaaa   1200
ggaatgtggt ctcttagatc tgctactgat gatccatatg acacattctt ggttgttagc   1260
ttcattagtg agacacgcgt tttggctatg aaccttgagg atgagctgga agaaactgag   1320
atagaaggct tcaattctca agtccagacc ttgttttgtc atgatgctgt atacaaccag   1380
cttgttcagg ttacttcaaa ttctgttaga ttggtcagtt ctacctctag agatctgaaa   1440
aacgagtggt ttgccccagt cggctactcg gtcaatgttg caactgctaa tgccactcag   1500
gtactattgg ctactggggg tggccatctg gtatacctag aaattggtga tggggtgttg   1560
aatgaagtaa aatatgccaa gttggattat gatatctcgt gcctggacat aaatccaatt   1620
ggtgaaaatc cgaactacag taacattgca gcagttggaa tgtggacaga cataagtgtc   1680
aggatatatt cacttcctga cttgaatctc attacaaagg aacagctagg aggggagata   1740
attcctcgtt ctgttctgat gtgttccttc gaagggatat cttatctact atgtgctttg   1800
ggagatggcc atctcttgaa ttttgtattg agcatgagta ctggtgagct gacagatagg   1860
aaaaaagttt ctcttgggac acagcccata acacttcgta cattctcatc taaagatact   1920
acacatgtct ttgctgcctc cgataggcca acagttattt acagcagtaa caagaagctg   1980
ctttatagca atgtaaatct aaaagaagtt agtcatatgt gcccattcaa tgttgcagct   2040
tttccagaca gccttgcaat cgctaaagaa ggtgagttaa caattggcac tattgatgaa   2100
attcaaaagc ttcacattcg ttcaataccc cttggggagc atgcacgtcg catcagccat   2160
caagagcaga cccggacatt tgctctatgc agtgtgaagt atactcagtc aaatgcagat   2220
gatcctgaaa tgcattttgt ccgcctgttg gatgatcaga catttgagtt catatcaaca   2280
tatcccctttg accaatttga atatggctgt tccatactaa gctgctcctt ttctgatgat   2340
agtaatgtgt attattgcat tggaactgca tatgtgatgc cagaggaaaa tgaacctact   2400
aagggccgaa ttttagtttt tatagttgaa gatggaaagc tccagctaat tgctgagaag   2460
gaaactaagg gagctgtcta ctctctaaat gccttcaatg gaaactgct tgctgcaatc   2520
aatcagaaga ttcaattgta caagtgggct tcgcgtgagg atggtggcag ccgagaattg   2580
cagacagaat gtggacacca tggtcatata ttagctcttt atgttcaaac acgtgggat   2640
ttcattgttg ttggtgattt gatgaaatcc atttctctgc tgattttcaa gcatgaagag   2700
ggtgctatag aggagcgagc cagagactat aatgcaaatt ggatgtcagc tgttgagatt   2760
ctcgatgatg acatttatct tggtgctgag aataacttca accttttcac ggtcaggaaa   2820
aatagtgaag gtgctacaga tgaggagcgc agccgtcttg aagtggttgg tgaataccac   2880
cttggcgaat tgttaatag gtttagacat ggttcacttg tcatgcgact accagattca   2940
gatgttgggc agatacccac tgtcatattt ggcacagtga atggtgttat aggggtgatt   3000
gcatcactac ctcatgatca atatttattt ttggagaagc tgcagacaaa cttacggaaa   3060
```

```
gtgataaagg gtgtgggagg tctgagccat gagcagtgga ggtcgtttta caatgagaag    3120
aaaacagtag atgctaaaaa ctttcttgat ggagatttga ttgaatcatt cctagatctt    3180
agcaggaata ggatggaaga gatttcaaag gctatgtcag ttccagttga ggaactaatg    3240
aagagagtgg aagagttgac aaggttgcat tag                                 3273

<210> SEQ ID NO 2
<211> LENGTH: 3273
<212> TYPE: DNA
<213> ORGANISM: Lycopersicon esculentum

<400> SEQUENCE: 2
atgagtgtat ggaactacgt ggttacggct cacaaaccaa caaatgttac acattcctgt      60
gttggcaatt tcaccggtcc tcaagagctc aatcttatca ttgcgaaatg tactcgaatc     120
gagattcatt tacttactcc ccaaggttta cagcctatgt tagatgtgcc aatatatggg     180
aggatcgcga cacttgagct ttttcgtcct cacggtgaaa cacaagatct tctcttcatc     240
gcaacagagc gatataaatt ctgtgtcctt caatgggata ctgaggcatc tgaagttatc     300
acaagagcaa tgggagatgt gtcagaccga ataggccgtc ccacagataa tggtcagatt     360
ggtataattg atccagattg cagattgatc gggctacatc tttatgatgg actatttaag     420
gttattccat ttgataacaa aggccaactg aaggaagctt taacatcag gctcgaggag      480 cttcaagttt tagatattaa attcttgtat ggttgcccaa agcctacaat tgttgttcta     540
tatcaggata caaggatgc ccggcatgtc aaaacatatg aggtgtcctt gaaagacaaa      600
gattttattg aagggccatg ggctcaaaat aatcttgata tggagcttc tttgctaata     660 ccagtacctc caccactgtg tggtgtattg attattggag aagaaccat cgtttattgc     720 agcgcttcag cttttaaggc tatcccaatt agaccttcta tcacaagagc atatgggcgg     780
gttgatgctg atggttctcg atatttgctt ggggatcata tgggcttct tcacctactt     840 gtaatcactc atgagaagga gaaagttacc ggactcaaaa ttgagctact gggggaaact     900
tctattgcat caaccatatc ataccctagac aatgcttttg tcttcattgg ctcaagctac     960
ggagattcac agcttgtaaa gctcaatctc cagcctgaca ccaaaggttc ttatgtggaa    1020
gttctagaga gatatgtcaa tttaggacct attgtggact tctgtgttgt tgatctggaa    1080
aggcaaggtc aaggtcaggt tgtaacttgc tctggagcct ataaggatgg atcacttcgt    1140
attgttcgaa atggaattgg cataaatgaa caggcgtctg tggaactaca agggatcaaa    1200
ggaatgtggt ctcttagatc tgctactgat gatccatatg acacattctt ggttgttagc    1260
ttcattagtg agacacgcgt tttggctatg aaccttgagg atgagctgga agaaactgag    1320
atagaaggct tcaattctca agtccagacc ttgttttgtc atgatgctgt atacaaccag    1380
cttgttcagg ttacttcaaa ttctgttaga ttggtcagtt ctacctctag agatctgaaa    1440
aacgagtggt tgccccagt cggctactcg gtcaatgttg caactgctaa tgccactcag    1500
gtactattgg ctactggggg tggccatctg gtatacctag aaattggtga tggggtgttg    1560
aatgaagtaa atatgccaa gttggattat gatatctcgt gcctggacat aaatccaatt    1620
ggtgaaaatc cgaactacag taacattgca gcagttgaa tgtggacaga cataagtgtc    1680
aggatatatt cacttcctga cttgaatctc attacaaagg aacagctagg aggggagata    1740
attcctcgtt ctgttctgat gtgttccttc gaagggatat cttatctact atgtgctttg    1800
ggagatggcc atctcttgaa ttttgtattg agcatgagta ctggtgagct gacagatagg    1860
aaaaaagttt ctcttgggac acagcccata acacttcgta cattctcatc taaagatact    1920
```

| | |
|---|---|
| acacatgtct tgctgcctc cgataggcca acagttattt acagcagtaa caagaagctg | 1980 |
| ctttatagca atgtaaatct aaaagaagtt agtcatatgt gcccattcaa tgttgcagct | 2040 |
| tttccagaca gccttgcaat cgctaaagaa ggtgagttaa caattggcac tattgatgaa | 2100 |
| attcaaaagc ttcacattcg ttcaataccc cttggggagc atgcacgtcg catcagccat | 2160 |
| caagagcaga cccggacatt tgctctatgc agtgtgaagt atactcagtc aaatgcagat | 2220 |
| gatcctgaaa tgcattttgt ccgcctgttg gatgatcaga catttgagtt catatcaaca | 2280 |
| tatccccttg accaatttga atatggctgt tccatactaa gctgctcctt ttctgatgat | 2340 |
| agtaatgtgt attattgcat tggaactgca tatgtgatgc cagaggaaaa taaacctact | 2400 |
| aagggccgaa ttttagtttt tatagttgaa gatggaaagc tccagctaat tgctgagaag | 2460 |
| gaaactaagg gagctgtcta ctctctaaat gccttcaatg ggaaactgct tgctgcaatc | 2520 |
| aatcagaaga ttcaattgta caagtgggct tcgcgtgagg atggtggcag ccgagaattg | 2580 |
| cagacagaat gtggacacca tggtcatata ttagctcttt atgttcaaac acgtggggat | 2640 |
| ttcattgttg ttggtgattt gatgaaatcc atttctctgc tgattttcaa gcatgaagag | 2700 |
| ggtgctatag aggagcgagc cagagactat aatgcaaatt ggatgtcagc tgttgagatt | 2760 |
| ctcgatgatg acatttatct tggtgctgag aataacttca acctttttcac ggtcaggaaa | 2820 |
| aatagtgaag gtgctacaga tgaggagcgc agccgtcttg aagtggttgg tgaataccac | 2880 |
| cttggcgaat ttgttaatag gtttagacat ggttcacttg tcatgcgact accagattca | 2940 |
| gatgttgggc agatacccac tgtcatattt ggcacagtga atggtgttat agggtgatt | 3000 |
| gcatcactac ctcatgatca atatttattt ttggagaagc tgcagacaaa cttacggaaa | 3060 |
| gtgataaagg gtgtgggagg tctgagccat gagcagtgga ggtcgtttta caatgagaag | 3120 |
| aaaacagtag atgctaaaaa cttcttgat ggagatttga ttgaatcatt cctagatctt | 3180 |
| agcaggaata ggatggaaga gatttcaaag gctatgtcag ttccagttga ggaactaatg | 3240 |
| aagagagtgg aagagttgac aaggttgcat tag | 3273 |

<210> SEQ ID NO 3
<211> LENGTH: 22
<212> TYPE: DNA
<213> ORGANISM: Artificial Sequence
<220> FEATURE:
<223> OTHER INFORMATION: Synthetic

<400> SEQUENCE: 3
acgacctatc gtggacttct gt            22

<210> SEQ ID NO 4
<211> LENGTH: 22
<212> TYPE: DNA
<213> ORGANISM: Artificial Sequence
<220> FEATURE:
<223> OTHER INFORMATION: Synthetic

<400> SEQUENCE: 4
ctggacttga gaattgaagc ct            22

<210> SEQ ID NO 5
<211> LENGTH: 21
<212> TYPE: DNA
<213> ORGANISM: Artificial Sequence
<220> FEATURE:
<223> OTHER INFORMATION: Synthetic

<400> SEQUENCE: 5

```
gagcctataa ggatggatca c                                              21

<210> SEQ ID NO 6
<211> LENGTH: 21
<212> TYPE: DNA
<213> ORGANISM: Artificial Sequence
<220> FEATURE:
<223> OTHER INFORMATION: Synthetic

<400> SEQUENCE: 6
cagcagttgg aatgtggaca g                                              21

<210> SEQ ID NO 7
<211> LENGTH: 22
<212> TYPE: DNA
<213> ORGANISM: Artificial Sequence
<220> FEATURE:
<223> OTHER INFORMATION: Synthetic

<400> SEQUENCE: 7
gcaatcgcta aagaaggtga gt                                             22

<210> SEQ ID NO 8
<211> LENGTH: 22
<212> TYPE: DNA
<213> ORGANISM: Artificial Sequence
<220> FEATURE:
<223> OTHER INFORMATION: Synthetic

<400> SEQUENCE: 8
gcattatagt ctctggctcg ct                                             22

<210> SEQ ID NO 9
<211> LENGTH: 20
<212> TYPE: DNA
<213> ORGANISM: Artificial Sequence
<220> FEATURE:
<223> OTHER INFORMATION: Synthetic

<400> SEQUENCE: 9
ggacatttgc tctatgcagt                                                20

<210> SEQ ID NO 10
<211> LENGTH: 22
<212> TYPE: DNA
<213> ORGANISM: Artificial Sequence
<220> FEATURE:
<223> OTHER INFORMATION: Synthetic

<400> SEQUENCE: 10
aggcatttag agagtagaca gc                                             22

<210> SEQ ID NO 11
<211> LENGTH: 20
<212> TYPE: DNA
<213> ORGANISM: Artificial Sequence
<220> FEATURE:
<223> OTHER INFORMATION: Synthetic

<400> SEQUENCE: 11
tttggagaag ctgcagacaa                                                20

<210> SEQ ID NO 12
<211> LENGTH: 22
<212> TYPE: DNA
<213> ORGANISM: Artificial Sequence
<220> FEATURE:
```

<223> OTHER INFORMATION: Synthetic

<400> SEQUENCE: 12
cacaacctca cagaagaaga ag                                                 22

<210> SEQ ID NO 13
<211> LENGTH: 22
<212> TYPE: DNA
<213> ORGANISM: Artificial Sequence
<220> FEATURE:
<223> OTHER INFORMATION: Synthetic

<400> SEQUENCE: 13
ccactctctt cattagttcc tc                                                 22

<210> SEQ ID NO 14
<211> LENGTH: 22
<212> TYPE: DNA
<213> ORGANISM: Artificial Sequence
<220> FEATURE:
<223> OTHER INFORMATION: Synthetic

<400> SEQUENCE: 14
gtaatacgac tcactatagg gc                                                 22

<210> SEQ ID NO 15
<211> LENGTH: 22
<212> TYPE: DNA
<213> ORGANISM: Artificial Sequence
<220> FEATURE:
<223> OTHER INFORMATION: Synthetic

<400> SEQUENCE: 15
atagcgggaa gagggaagat ac                                                 22

<210> SEQ ID NO 16
<211> LENGTH: 22
<212> TYPE: DNA
<213> ORGANISM: Artificial Sequence
<220> FEATURE:
<223> OTHER INFORMATION: Synthetic

<400> SEQUENCE: 16
tgttttccag agttaccgga ct                                                 22

<210> SEQ ID NO 17
<211> LENGTH: 22
<212> TYPE: DNA
<213> ORGANISM: Artificial Sequence
<220> FEATURE:
<223> OTHER INFORMATION: Synthetic

<400> SEQUENCE: 17
tagcttgagc caatgaagac aa                                                 22

<210> SEQ ID NO 18
<211> LENGTH: 16
<212> TYPE: DNA
<213> ORGANISM: Artificial Sequence
<220> FEATURE:
<223> OTHER INFORMATION: Synthetic

<400> SEQUENCE: 18
atgaagacaa aagcat                                                        16

<210> SEQ ID NO 19

<211> LENGTH: 467
<212> TYPE: DNA
<213> ORGANISM: Artificial Sequence
<220> FEATURE:
<223> OTHER INFORMATION: Synthetic

<400> SEQUENCE: 19

| | | | | | | |
|---|---|---|---|---|---|---|
| ctcatgagaa | ggagaagtgc | gtcagcattt | tctagactgt | catttctact | ttagctgagt | 60 |
| tgctgggaat | gaaatcttct | cttgtacccc | tgcctggttg | ctggaataaa | aatgtttaat | 120 |
| ttggattgtt | aacctgtttt | ccagagttac | cggactcaaa | attgagctac | tgggggaaac | 180 |
| ttctattgca | tcaaccatat | catacctaga | cwatgctttt | gtcttcattg | gctcaagcta | 240 |
| cggagattca | caggtacttt | taactgttga | gtgcatcttg | gtgcaataag | ttggtttta | 300 |
| gagctgcctt | attgtatttt | ccatacagta | gcctttcatt | catttggaac | attgaggttt | 360 |
| taaatttcag | ttgcctattt | ctggtggtgc | ttcatatttc | acagttccac | taatattttt | 420 |
| gaattcacgt | ttagcttgta | aagctcaatc | tccagcctga | caccaaa | | 467 |

<210> SEQ ID NO 20
<211> LENGTH: 55
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Arabidopsis DDB1A hp-1

<400> SEQUENCE: 20

Ile Thr Glu Lys Glu Lys Val Thr Gly Leu Lys Ile Glu Leu Leu Gly
1               5                   10                  15

Glu Thr Ser Ile Ala Ser Thr Ile Ser Tyr Leu Asp Asn Ala Val Val
            20                  25                  30

Phe Val Gly Ser Ser Tyr Gly Asp Ser Gln Leu Val Lys Leu Leu Asn
        35                  40                  45

Leu His Pro Asp Ala Lys Gly
    50                  55

<210> SEQ ID NO 21
<211> LENGTH: 59
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Arabidopsis DDB1A hp-1W

<400> SEQUENCE: 21

Leu Ser Cys Ser Phe Thr Glu Asp Lys Asn Val Tyr Cys Val Gly
1               5                   10                  15

Thr Ala Tyr Val Leu Pro Glu Glu Asn Glu Pro Thr Lys Gly Arg Ile
            20                  25                  30

Leu Val Phe Ile Val Glu Asp Gly Arg Leu Gln Leu Ile Ala Glu Lys
        35                  40                  45

Glu Thr Lys Gly Ala Val Tyr Ser Leu Asn Ala
    50                  55

<210> SEQ ID NO 22
<211> LENGTH: 55
<212> TYPE: PRT
<213> ORGANISM: Artificial Sequence
<220> FEATURE:

```
<223> OTHER INFORMATION: Synthetic
<220> FEATURE:
<221> NAME/KEY: misc_feature
<223> OTHER INFORMATION: Arabidopsis DDB1B hp-1

<400> SEQUENCE: 22

Ile Thr His Glu Lys Glu Lys Val Thr Gly Leu Lys Ile Glu Leu Leu
1               5                   10                  15

Gly Glu Thr Ser Ile Ala Ser Ser Ile Ser Tyr Leu Asp Asn Ala Val
            20                  25                  30

Val Phe Val Gly Ser Ser Tyr Gly Asp Ser Gln Leu Ile Lys Leu Asn
        35                  40                  45

Leu Gln Pro Asp Ala Lys Gly
    50                  55

<210> SEQ ID NO 23
<211> LENGTH: 59
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Arabidopsis DDB1B hp-1W

<400> SEQUENCE: 23

Leu Ser Cys Ser Phe Thr Asp Asp Lys Asn Val Tyr Tyr Cys Val Gly
1               5                   10                  15

Thr Ala Tyr Val Leu Pro Glu Glu Asn Glu Pro Thr Lys Gly Arg Ile
            20                  25                  30

Leu Val Phe Ile Val Glu Glu Gly Arg Leu Gln Leu Ile Thr Glu Lys
        35                  40                  45

Glu Thr Lys Gly Ala Val Tyr Ser Leu Asn Ala
    50                  55

<210> SEQ ID NO 24
<211> LENGTH: 55
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: tomato cv. Ailsa Craig hp-1

<400> SEQUENCE: 24

Ile Thr His Glu Lys Glu Lys Val Thr Gly Leu Lys Ile Glu Leu Leu
1               5                   10                  15

Gly Glu Thr Ser Ile Ala Ser Thr Ile Ser Tyr Leu Asp Asn Ala Phe
            20                  25                  30

Val Phe Ile Gly Ser Ser Tyr Gly Asp Ser Gln Leu Val Lys Leu Asn
        35                  40                  45

Leu Gln Pro Asp Thr Lys Gly
    50                  55

<210> SEQ ID NO 25
<211> LENGTH: 59
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: tomato cv. Ailsa Craig hp-1W
```

<400> SEQUENCE: 25

Leu Ser Cys Ser Phe Ser Asp Asp Ser Asn Val Tyr Tyr Cys Ile Gly
1               5                   10                  15

Thr Ala Tyr Val Met Pro Glu Glu Asn Glu Pro Thr Lys Gly Arg Ile
            20                  25                  30

Leu Val Phe Ile Val Glu Asp Gly Lys Leu Gln Leu Ile Ala Glu Lys
        35                  40                  45

Glu Thr Lys Gly Ala Val Tyr Ser Leu Asn Ala
    50                  55

<210> SEQ ID NO 26
<211> LENGTH: 55
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: rice hp-1

<400> SEQUENCE: 26

Leu Thr His Glu Arg Glu Arg Val Thr Gly Leu Lys Ile Glu Tyr Leu
1               5                   10                  15

Gly Glu Thr Ser Ile Ala Ser Ser Ile Ser Tyr Leu Asp Asn Gly Val
            20                  25                  30

Val Tyr Val Gly Ser Arg Phe Gly Asp Ser Gln Leu Val Lys Leu Asn
        35                  40                  45

Leu Gln Ala Asp Pro Asn Gly
    50                  55

<210> SEQ ID NO 27
<211> LENGTH: 59
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: rice hp-1W

<400> SEQUENCE: 27

Ile Ser Cys Ser Phe Ser Asp Asp Asn Asn Val Tyr Tyr Cys Val Gly
1               5                   10                  15

Thr Ala Tyr Val Leu Pro Glu Glu Asn Glu Pro Ser Lys Gly Arg Ile
            20                  25                  30

Leu Val Phe Ala Val Glu Asp Gly Arg Leu Gln Leu Ile Val Glu Lys
        35                  40                  45

Glu Thr Lys Gly Ala Val Tyr Ser Leu Asn Ala
    50                  55

<210> SEQ ID NO 28
<211> LENGTH: 60
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: human hp-1

<400> SEQUENCE: 28

Leu Glu Lys Glu Glu Gln Met Asp Gly Thr Val Thr Leu Lys Asp Leu
1               5                   10                  15

```
Arg Val Glu Leu Leu Gly Glu Thr Ser Ile Ala Glu Cys Leu Thr Tyr
            20                  25                  30

Leu Asp Asn Gly Val Val Phe Val Gly Ser Arg Leu Gly Asp Ser Gln
        35                  40                  45

Leu Val Lys Leu Asn Val Asp Ser Asn Glu Gln Gly
    50                  55                  60

<210> SEQ ID NO 29
<211> LENGTH: 59
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: human hp-1W

<400> SEQUENCE: 29

Val Ser Cys Lys Leu Gly Lys Asp Pro Asn Thr Tyr Phe Ile Val Gly
1               5                   10                  15

Thr Ala Met Val Tyr Pro Glu Glu Ala Glu Pro Lys Gln Gly Arg Ile
            20                  25                  30

Val Val Phe Gln Tyr Ser Asp Gly Lys Leu Gln Thr Val Ala Glu Lys
        35                  40                  45

Glu Val Lys Gly Ala Val Tyr Ser Met Val Glu
    50                  55

<210> SEQ ID NO 30
<211> LENGTH: 58
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Drosophila hp-1

<400> SEQUENCE: 30

Leu Gly Thr Ala Glu Thr Ser Lys Gly Val Thr Val Lys Asp Ile Lys
1               5                   10                  15

Val Glu Gln Leu Gly Glu Ile Ser Ile Pro Glu Cys Ile Thr Tyr Leu
            20                  25                  30

Asp Asn Gly Phe Leu Tyr Ile Gly Ala Arg His Gly Asp Ser Gln Leu
        35                  40                  45

Val Arg Leu Asn Ser Glu Ala Ile Asp Gly
    50                  55

<210> SEQ ID NO 31
<211> LENGTH: 59
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Drosophila hp-1W

<400> SEQUENCE: 31

Met Ser Ala Lys Leu Gly Asp Asp Pro Asn Thr Tyr Tyr Val Val Ala
1               5                   10                  15

Thr Ser Leu Val Ile Pro Glu Glu Pro Glu Pro Lys Val Gly Arg Ile
            20                  25                  30

Ile Ile Phe His Tyr His Glu Asn Lys Leu Thr Gln Val Ala Glu Thr
        35                  40                  45
```

```
Lys Val Asp Gly Thr Cys Tyr Ala Leu Val Glu
     50                  55

<210> SEQ ID NO 32
<211> LENGTH: 60
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: chicken hp-1

<400> SEQUENCE: 32

Leu Glu Lys Glu Glu Gln Met Asp Gly Thr Val Thr Leu Lys Asp Leu
1               5                   10                  15

Arg Val Glu Leu Leu Gly Glu Thr Ser Ile Ala Glu Cys Leu Thr Tyr
            20                  25                  30

Leu Asp Asn Gly Val Val Phe Val Gly Ser Arg Leu Gly Asp Ser Gln
        35                  40                  45

Leu Val Lys Leu Asn Val Asp Ser Asn Glu Gln Gly
    50                  55                  60

<210> SEQ ID NO 33
<211> LENGTH: 59
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: chicken hp-1W

<400> SEQUENCE: 33

Val Ser Cys Lys Leu Gly Lys Asp Pro Asn Thr Tyr Phe Ile Val Gly
1               5                   10                  15

Thr Ala Met Val Tyr Pro Glu Glu Ala Glu Pro Lys Gln Gly Arg Ile
            20                  25                  30

Val Val Phe His Tyr Ser Asp Gly Lys Leu Gln Ser Leu Ala Glu Lys
        35                  40                  45

Glu Val Lys Gly Ala Val Tyr Ser Met Val Glu
    50                  55

<210> SEQ ID NO 34
<211> LENGTH: 53
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: S. pombe hp-1

<400> SEQUENCE: 34

Ala Leu Phe Thr Asp Glu Thr Val Ser Met Glu Leu Glu Lys Leu Gly
1               5                   10                  15

Glu Ser Ser Ile Ala Ser Cys Leu Ile Ala Leu Pro Asp Asn His Leu
            20                  25                  30

Phe Val Gly Ser His Phe Asn Asn Ser Val Leu Leu Gln Leu Pro Ser
        35                  40                  45

Ile Thr Lys Asn Asn
    50
```

```
<210> SEQ ID NO 35
<211> LENGTH: 56
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: S. pombe hp-1W

<400> SEQUENCE: 35

Ile Leu Met Asn Asp Asp Lys Arg Val Val Val Gly Thr Gly Phe Asn
1               5                   10                  15

Phe Pro Asp Gln Asp Ala Pro Asp Ser Gly Arg Leu Met Val Phe Glu
            20                  25                  30

Met Thr Ser Asp Asn Asn Ile Glu Met Gln Ala Glu His Lys Val Gln
        35                  40                  45

Gly Ser Val Asn Thr Leu Val Leu
    50                  55

<210> SEQ ID NO 36
<211> LENGTH: 3273
<212> TYPE: DNA
<213> ORGANISM: Artificial Sequence
<220> FEATURE:
<223> OTHER INFORMATION: Synthetic

<400> SEQUENCE: 36
atgagtgtat ggaactacgt ggttacgggct cacaaaccaa caaatgttac acattcctgt    60
gttggcaatt tcaccggtcc tcaagagctc aatcttatca ttgcgaaatg tactcgaatc   120
gagattcatt tacttactcc ccaaggttta cagcctatgt tagatgtgcc aatatatggg   180
aggatcgcga cacttgagct ttttcgtcct cacggtgaaa cacaagatct tctcttcatc   240
gcaacagagc gatataaatt ctgtgtcctt caatgggata ctgaggcatc tgaagttatc   300
acaagagcaa tgggagatgt gtcagaccga ataggccgtc ccacagataa tggtcagatt   360
ggtataattg atccagattg cagattgatc gggctacatc tttatgatgg actatttaag   420
gttattccat ttgataacaa aggccaactg aaggaagctt ttaacatcag gctcgaggag   480
cttcaagttt tagatattaa attcttgtat ggttgcccaa agcctacaat tgttgttcta   540
tatcaggata caaggatgcc ccggcatgtc aaaacatatg aggtgtcctt gaaagacaaa   600 gatttttattg aagggccatg ggctcaaaat aatcttgata tggagcttc tttgctaata   660 ccagtacctc caccactgtg tggtgtattg attattggag aagaaccat cgtttattgc   720 agcgcttcag ctttttaaggc tatcccaatt agaccttcta tcacaagagc atatgggcgg   780 ttgatgctg atggttctcg atatttgctt ggggatcata tgggcttct tcacctactt   840 gtaatcactc atgagaagga gaaagttacc ggactcaaaa ttgagctact ggggaaact   900 tctattgcat caaccatatc ataccctagac aatgcttttg tcttcattgg ctcaagctac   960
ggagattcac agcttgtaaa gctcaatctc cagcctgaca ccaaaggttc ttatgtggaa  1020
gttctagaga gatatgtcaa tttaggacct attgtggact tctgtgttgt tgatctggaa  1080
aggcaaggtc aaggtcaggt tgtaacttgc tctggagcct ataaggatgg atcacttcgt  1140
attgttcgaa atggaattgg cataaatgaa caggcgtctg tggaactaca agggatcaaa  1200
ggaatgtggt ctcttagatc tgctactgat gatccatatg acacattctt ggttgttagc  1260
ttcattagtg agacacgcgt tttggctatg aaccttgagg atgagctgga agaaactgag  1320
atagaaggct tcaattctca agtccagacc ttgttttgtc atgatgctgt atacaaccag  1380
```

```
cttgttcagg ttacttcaaa ttctgttaga ttggtcagtt ctacctctag agatctgaaa    1440
aacgagtggt ttgccccagt cggctactcg gtcaatgttg caactgctaa tgccactcag    1500
gtactattgg ctactggggg tggccatctg gtatacctag aaattggtga tggggtgttg    1560
aatgaagtaa aatatgccaa gttggattat gatatctcgt gcctggacat aaatccaatt    1620
ggtgaaaatc cgaactacag taacattgca gcagttggaa tgtggacaga cataagtgtc    1680
aggatatatt cacttcctga cttgaatctc attacaaagg aacagctagg aggggagata    1740
attcctcgtt ctgttctgat gtgttccttc gaagggatat cttatctact atgtgctttg    1800
ggagatggcc atctcttgaa ttttgtattg agcatgagta ctggtgagct gacagatagg    1860
aaaaaagttt ctcttgggac acagcccata acacttcgta cattctcatc taaagatact    1920
acacatgtct ttgctgcctc cgataggcca acagttattt acagcagtaa caagaagctg    1980
ctttatagca atgtaaatct aaaagaagtt agtcatatgt gcccattcaa tgttgcagct    2040
tttccagaca gccttgcaat cgctaaagaa ggtgagttaa caattggcac tattgatgaa    2100
attcaaaagc ttcacattcg ttcaataccc cttggggagc atgcacgtcg catcagccat    2160
caagagcaga cccggacatt tgctctatgc agtgtgaagt atactcagtc aaatgcagat    2220
gatcctgaaa tgcattttgt ccgcctgttg gatgatcaga catttgagtt catatcaaca    2280
tatccccttg accaatttga atatggctgt tccatactaa gctgctcctt ttctgatgat    2340
agtaatgtgt attattgcat tggaactgca tatgtgatgc cagaggaaaa tgaacctact    2400
aagggccgaa tttttagttttt tatagttgaa gatggaaagc tccagctaat tgctgagaag    2460
gaaactaagg gagctgtcta ctctctaaat gccttcaatg ggaaactgct tgctgcaatc    2520
aatcagaaga ttcaattgta caagtgggct tcgcgtgagg atggtggcag ccgagaattg    2580
cagacagaat gtggacacca tggtcatata ttagctcttt atgttcaaac acgtggggat    2640
ttcattgttg ttggtgattt gatgaaatcc atttctctgc tgattttcaa gcatgaagag    2700
ggtgctatag aggagcgagc cagagactat aatgcaaatt ggatgtcagc tgttgagatt    2760
ctcgatgatg acatttatct tggtgctgag aataacttca acctttttcac ggtcaggaaa    2820 aatagtgaag gtgctacaga tgaggagcgc agccgtcttg aagtggttgg tgaataccac    2880
cttggcgaat ttgttaatag gtttagacat ggttcacttg tcatgcgact accagattca    2940
gatgttgggc agatacccac tgtcatattt ggcacagtga atggtgttat aggggtgatt    3000
gcatcactac ctcatgatca atatttattt ttggagaagc tgcagacaaa cttacggaaa    3060
gtgataaagg gtgtgggagg tctgagccat gagcagtgga ggtcgtttta caatgagaag    3120
aaaacagtag atgctaaaaa ctttcttgat ggagatttga ttgaatcatt cctagatctt    3180
agcaggaata ggatggaaga gatttcaaag gctatgtcag ttccagttga ggaactaatg    3240
aagagagtgg aagagttgac aaggttgcat tag                                 3273
```

<210> SEQ ID NO 37
<211> LENGTH: 1090
<212> TYPE: PRT
<213> ORGANISM: Artificial Sequence
<220> FEATURE:
<223> OTHER INFORMATION: Synthetic

<400> SEQUENCE: 37

```
Met Ser Val Trp Asn Tyr Val Val Thr Ala His Lys Pro Thr Asn Val
 1               5                  10                  15

Thr His Ser Cys Val Gly Asn Phe Thr Gly Pro Gln Glu Leu Asn Leu
            20                  25                  30
```

```
Ile Ile Ala Lys Cys Thr Arg Ile Glu Ile His Leu Leu Thr Pro Gln
         35                  40                  45
Gly Leu Gln Pro Met Leu Asp Val Pro Ile Tyr Gly Arg Ile Ala Thr
 50                  55                  60
Leu Glu Leu Phe Arg Pro His Gly Glu Thr Gln Asp Leu Leu Phe Ile
 65                  70                  75                  80
Ala Thr Glu Arg Tyr Lys Phe Cys Val Leu Gln Trp Asp Thr Glu Ala
                 85                  90                  95
Ser Glu Val Ile Thr Arg Ala Met Gly Asp Val Ser Asp Arg Ile Gly
                100                 105                 110
Arg Pro Thr Asp Asn Gly Gln Ile Gly Ile Asp Pro Asp Cys Arg
                115                 120                 125
Leu Ile Gly Leu His Leu Tyr Asp Gly Leu Phe Lys Val Ile Pro Phe
130                 135                 140
Asp Asn Lys Gly Gln Leu Lys Glu Ala Phe Asn Ile Arg Leu Glu Glu
145                 150                 155                 160
Leu Gln Val Leu Asp Ile Lys Phe Leu Tyr Gly Cys Pro Lys Pro Thr
                165                 170                 175
Ile Val Val Leu Tyr Gln Asp Asn Lys Asp Ala Arg His Val Lys Thr
                180                 185                 190
Tyr Glu Val Ser Leu Lys Asp Lys Asp Phe Ile Glu Gly Pro Trp Ala
                195                 200                 205
Gln Asn Asn Leu Asp Asn Gly Ala Ser Leu Leu Ile Pro Val Pro Pro
210                 215                 220
Pro Leu Cys Gly Val Leu Ile Ile Gly Glu Thr Ile Val Tyr Cys
225                 230                 235                 240
Ser Ala Ser Ala Phe Lys Ala Ile Pro Ile Arg Pro Ser Ile Thr Arg
                245                 250                 255
Ala Tyr Gly Arg Val Asp Ala Asp Gly Ser Arg Tyr Leu Leu Gly Asp
                260                 265                 270
His Asn Gly Leu Leu His Leu Val Ile Thr His Glu Lys Glu Lys
                275                 280                 285
Val Thr Gly Leu Lys Ile Glu Leu Leu Gly Glu Thr Ser Ile Ala Ser
290                 295                 300
Thr Ile Ser Tyr Leu Asp Asn Ala Phe Val Phe Ile Gly Ser Ser Tyr
305                 310                 315                 320
Gly Asp Ser Gln Leu Val Lys Leu Asn Leu Gln Pro Asp Thr Lys Gly
                325                 330                 335
Ser Tyr Val Glu Val Leu Glu Arg Tyr Val Asn Leu Gly Pro Ile Val
                340                 345                 350
Asp Phe Cys Val Val Asp Leu Glu Arg Gln Gly Gln Gly Gln Val Val
                355                 360                 365
Thr Cys Ser Gly Ala Tyr Lys Asp Gly Ser Leu Arg Ile Val Arg Asn
370                 375                 380
Gly Ile Gly Ile Asn Glu Gln Ala Ser Val Glu Leu Gln Gly Ile Lys
385                 390                 395                 400
Gly Met Trp Ser Leu Arg Ser Ala Thr Asp Pro Tyr Asp Thr Phe
                405                 410                 415
Leu Val Val Ser Phe Ile Ser Glu Thr Arg Val Leu Ala Met Asn Leu
                420                 425                 430
Glu Asp Glu Leu Glu Glu Thr Glu Ile Glu Gly Phe Asn Ser Gln Val
                435                 440                 445
Gln Thr Leu Phe Cys His Asp Ala Val Tyr Asn Gln Leu Val Gln Val
                450                 455                 460
```

```
Thr Ser Asn Ser Val Arg Leu Val Ser Thr Ser Arg Asp Leu Lys
465                 470                 475                 480

Asn Glu Trp Phe Ala Pro Val Gly Tyr Ser Val Asn Val Ala Thr Ala
                    485                 490                 495

Asn Ala Thr Gln Val Leu Leu Ala Thr Gly Gly His Leu Val Tyr
            500                 505                 510

Leu Glu Ile Gly Asp Gly Val Leu Asn Glu Val Lys Tyr Ala Lys Leu
            515                 520                 525

Asp Tyr Asp Ile Ser Cys Leu Asp Ile Asn Pro Ile Gly Glu Asn Pro
530                 535                 540

Asn Tyr Ser Asn Ile Ala Ala Val Gly Met Trp Thr Asp Ile Ser Val
545                 550                 555                 560

Arg Ile Tyr Ser Leu Pro Asp Leu Asn Leu Ile Thr Lys Glu Gln Leu
                565                 570                 575

Gly Gly Glu Ile Ile Pro Arg Ser Val Leu Met Cys Ser Phe Glu Gly
            580                 585                 590

Ile Ser Tyr Leu Leu Cys Ala Leu Gly Asp Gly His Leu Leu Asn Phe
    595                 600                 605

Val Leu Ser Met Ser Thr Gly Glu Leu Thr Asp Arg Lys Lys Val Ser
610                 615                 620

Leu Gly Thr Gln Pro Ile Thr Leu Arg Thr Phe Ser Ser Lys Asp Thr
625                 630                 635                 640

Thr His Val Phe Ala Ala Ser Asp Arg Pro Thr Val Ile Tyr Ser Ser
                645                 650                 655

Asn Lys Lys Leu Leu Tyr Ser Asn Val Asn Leu Lys Glu Val Ser His
                660                 665                 670

Met Cys Pro Phe Asn Val Ala Ala Phe Pro Asp Ser Leu Ala Ile Ala
                675                 680                 685

Lys Glu Gly Glu Leu Thr Ile Gly Thr Ile Asp Glu Ile Gln Lys Leu
            690                 695                 700

His Ile Arg Ser Ile Pro Leu Gly Glu His Ala Arg Arg Ile Ser His
705                 710                 715                 720

Gln Glu Gln Thr Arg Thr Phe Ala Leu Cys Ser Val Lys Tyr Thr Gln
                725                 730                 735

Ser Asn Ala Asp Asp Pro Glu Met His Phe Val Arg Leu Leu Asp Asp
            740                 745                 750

Gln Thr Phe Glu Phe Ile Ser Thr Tyr Pro Leu Asp Gln Phe Glu Tyr
            755                 760                 765

Gly Cys Ser Ile Leu Ser Cys Ser Phe Ser Asp Asp Ser Asn Val Tyr
    770                 775                 780

Tyr Cys Ile Gly Thr Ala Tyr Val Met Pro Glu Asn Glu Pro Thr
785                 790                 795                 800

Lys Gly Arg Ile Leu Val Phe Ile Val Glu Asp Gly Lys Leu Gln Leu
                805                 810                 815

Ile Ala Glu Lys Glu Thr Lys Gly Ala Val Tyr Ser Leu Asn Ala Phe
                820                 825                 830

Asn Gly Lys Leu Leu Ala Ala Ile Asn Gln Lys Ile Gln Leu Tyr Lys
            835                 840                 845

Trp Ala Ser Arg Glu Asp Gly Ser Arg Glu Leu Gln Thr Glu Cys
850                 855                 860

Gly His His Gly His Ile Leu Ala Leu Tyr Val Gln Thr Arg Gly Asp
865                 870                 875                 880

Phe Ile Val Val Gly Asp Leu Met Lys Ser Ile Ser Leu Leu Ile Phe
```

-continued

```
                885                  890                  895
Lys His Glu Glu Gly Ala Ile Glu Glu Arg Ala Arg Asp Tyr Asn Ala
            900                  905                  910

Asn Trp Met Ser Ala Val Glu Ile Leu Asp Asp Asp Ile Tyr Leu Gly
        915                  920                  925

Ala Glu Asn Asn Phe Asn Leu Phe Thr Val Arg Lys Asn Ser Glu Gly
    930                  935                  940

Ala Thr Asp Glu Glu Arg Ser Arg Leu Glu Val Val Gly Glu Tyr His
945                  950                  955                  960

Leu Gly Glu Phe Val Asn Arg Phe Arg His Gly Ser Leu Val Met Arg
                965                  970                  975

Leu Pro Asp Ser Asp Val Gly Gln Ile Pro Thr Val Ile Phe Gly Thr
            980                  985                  990

Val Asn Gly Val Ile Gly Val Ile Ala Ser Leu Pro His Asp Gln Tyr
        995                  1000                 1005

Leu Phe Leu Glu Lys Leu Gln  Thr Asn Leu Arg Lys  Val Ile Lys
    1010                 1015                 1020

Gly Val Gly Gly Leu Ser His  Glu Gln Trp Arg Ser  Phe Tyr Asn
    1025                 1030                 1035

Glu Lys Lys Thr Val Asp Ala  Lys Asn Phe Leu Asp  Gly Asp Leu
    1040                 1045                 1050

Ile Glu Ser Phe Leu Asp Leu  Ser Arg Asn Arg Met  Glu Glu Ile
    1055                 1060                 1065

Ser Lys Ala Met Ser Val Pro  Val Glu Glu Leu Met  Lys Arg Val
    1070                 1075                 1080

Glu Glu Leu Thr Arg Leu His
    1085                 1090
```

US 8,420,322 B2

ISOLATED NUCLEOTIDE SEQUENCES RESPONSIBLE FOR THE TOMATO HIGH PIGMENT-1 MUTANT PHENOTYPE (HP-1) AND USES THEREOF

FIELD OF THE INVENTION

The present invention relates to modified nucleotide sequences that are responsible for producing the high pigment-1 and high pigment-$1^w$ phenotypes in tomatoes. More specifically, the present invention discloses point mutations within the tomato homolog of the *Arabidopsis thaliana* and human DDB1 (UV damaged DNA binding protein 1) gene, and the uses of said modified nucleotide sequences.

BACKGROUND OF THE INVENTION

Plants respond to light intensity, direction, duration, and spectral quality by modulating their developmental processes in an array of interactions that are referred to as photomorphogenesis. Photomorphogenic mutants have been proven to be an excellent tool in research of the complex interactions between light and plant development and some of them have also been used in several agricultural crop breeding programs. Photomorphogenic mutants have been reported in a number of species, including *Arabidopsis, Sorghum, Brassica*, tobacco, tomato and pea. In general, these mutants may be classified either as defective in photoreceptors, or altered in some aspect of light signal transduction chain (Chory, 1993).

Several photomorphogenic mutants have been described in tomato (*lycopersicon esculentum*). Among these, mutants carrying the monogenic recessive high pigment (hp-1, hp-$1^w$, hp-2, and hp-$2^j$) and dark green (dg) mutations are characterized by their exaggerated light responsiveness.

These mutants display higher anthocyanin levels, shorter hypocotyls, and greater fruit pigmentation in comparison to their semi-isogenic wild type plants (Mochizuki and Kamimura 1984; Wann et al. 1985). The increased fruit pigmentation seen in these mutants is due to significantly elevated levels of carotenoids, primarily lycopene, and flavonoids in the mature ripe red fruit. As a consequence of their effect on fruit color, hp and dg mutations were introgressed into several commercial processing and fresh-market tomato cultivars that are currently marketed as Lycopene Rich Tomatoes (LRT) (Wann, 1997).

The hp-1 mutant was originally discovered as a spontaneous mutant in 1917 at the Campbell Soup Company farms (Riverton, N.J.) (Reynard, 1956), The hp-$1^w$ mutant appeared among progeny of a plant raised from ethyl methanesulfonate (EMS)-treated seeds of the genotype GT (Peters et al. 1989), the hp-2 mutant was reported in the Italian San Marzano variety in 1975 (Soressi 1975), the hp-$2^j$ mutant was found among progeny of a T-DNA-transformed plant (cv Moneymaker) (van Tuinen et al. 1997), and the dg mutant appeared in trellised planting of the Manapal variety (Konsler 1973). Despite some initial confusion, it is now clear that there are two HP genes—HP-1 and HP-2—in the tomato genome, that map to chromosomes 2 and 1, respectively (van Tuinen et al. 1997; Yen et al. 1997). (Van Tuinen et al. 1997; Yen et al. 1997). At each of these loci, two of the above mentioned mutant alleles have been initially identified: hp-1 and hp-$1^w$, hp-2 and hp-$2^j$ (Kerckhoff and Kendrick 1997; Van Tuinen et al. 1997).

WO 99/29866 discloses the cloning and sequencing of the HP-2 gene, said gene being found to encode the tomato homolog of the *Arabidopsis* nuclear protein DEETIOLATED1 (DET1).

This publication further discloses that a point mutation and deletion mutation, both of which are located in exon 11 at the 3' end of the coding sequence of HP-2, give rise to the previously-identified hp-$2^j$ and hp-2 mutants respectively. In the case of the hp-2 mutant, a point mutation directs alternative splicing of intron 10 that leads to a nine base pair deletion in exon 11.

Co-owned WO 03/57917 discloses another point mutation in the tomato homolog of the *Arabidopsis* DET1 gene that is responsible for the dg mutation, and which therefore comprises a $3^{rd}$ mutant allele at the HP-2 locus.

It is a purpose of the present invention to provide isolated nucleotide sequences containing the mutations responsible for the high pigment-1 (hp-1) and high pigment-$1^w$ (hp-$1^w$) photomorphogenic mutants of tomato plants.

It is a further purpose of the present invention to provide DNA markers that may be used as a molecular diagnostic tool for the identification and selection of hp-1 and hp-$1^w$ mutants.

A yet further purpose of the present invention is to provide molecular diagnostic tools that may be used for genotypic selection in the production of lycopene-enhancing double mutants.

Other purposes and advantages of the present invention will become apparent as the description proceeds.

SUMMARY OF THE INVENTION

It has now been found that the mutations responsible for both the hp-1 and hp-$1^w$ mutant phenotypes are located within the tomato homolog of the human and *Arabidopsis thaliana* UV DAMAGED DNA BINDING Protein 1 (DDB1) gene.

The present invention is primarily directed to isolated nucleotide sequences responsible for the tomato hp-1 and hp-$1^w$ phenotypes, wherein each of said sequences comprises an altered tomato DDB1 gene sequence or fragment or homolog thereof. In the case of the hp-1 mutation, the alteration in said sequence or fragment or homolog comprises a single $A^{931}$-to-$T^{931}$ base transversion in the tomato homolog of the DDB1 coding sequence. In the case of the hp-$1^w$ mutation, the alteration in said sequence or fragment or homolog comprises a single $G^{2392}$-to-$A^{2392}$ transition in the tomato homolog of the DDB1 coding sequence.

In one preferred embodiment of the present invention, the isolated nucleotide sequence encoding the hp-1 mutation comprises the sequence defined as SEQ ID NO:1 in the sequence listing. It is to be noted that all of the sequences contained in the enclosed sequence listing are to be considered to form an integral part of the present disclosure.

In another preferred embodiment of the present invention, the isolated nucleotide sequence encoding the hp-$1^w$ mutation comprises the sequence defined as SEQ ID NO:2 in the sequence listing.

It is to be understood that the present invention also includes within its scope all fragments of the above-defined sequences that encode the hp-1 and hp-$1^w$ mutations, wherein said fragments comprise the region of the DDB1 gene sequence containing the mutated nucleotide, that is, the region containing nucleotide 931 in the case of the hp-1 mutation, and nucleotide 2392 in the case of the hp-$1^w$ mutation.

The present invention is also directed to methods for detecting the presence of the hp-1 and (independently) the hp-$1^w$ mutations in plant material.

Thus, in one embodiment of this aspect, the present invention provides a method for detecting the presence of the hp-1 mutation in a plant, comprising the steps of isolating the genomic DNA from said plant, amplifying a gene fragment containing said hp-1 mutation from said genomic DNA by use of a PCR technique and determining the presence of said hp-1 mutation in said genomic DNA.

In another embodiment, the present invention provides a method for detecting the presence of the hp-1$^w$ mutation in a plant, comprising the steps of isolating the genomic DNA from said plant, amplifying a gene fragment containing said hp-1$^w$ mutation from said genomic DNA by use of a PCR technique and determining the presence of said hp-1$^w$ mutation in said genomic DNA Any suitable technique may be used to determine the presence of the hp-1 and (independently) the hp-1$^w$ mutations in the plant material. However, in a preferred embodiment, the presence of said mutations is determined by the use of a pyrosequencing technique, wherein the sequence data obtained from said technique is compared with the sequences defined in SEQ ID NO:1 (in the case of hp-1) and SEQ ID NO:2 (in the case of hp-1$^w$).

In a particularly preferred embodiment, the above-defined method of determining the presence of the hp-1 and (independently) the hp-1$^w$ mutations is applied to material obtained from the species *Lycopersicon esculentum*.

In one particularly preferred embodiment, the above-disclosed method of determining the presence of the hp-1 and (independently) the hp-1$^w$ mutations is used as a means of quality control, or post-control in seed production, for detecting the presence of the dg allele in cultivars and their parental lines. The term post-control is used herein to indicate quality control checks that are performed following seed production, in order to confirm the intended genotype of said seeds.

In another aspect, the present invention is also directed to a method for the determination of the presence of two different photomorphogenic mutations in a plant, wherein one of said mutations is either the hp-1 or the hp-1$^w$ mutation, comprising detecting the presence of a photomorphogenic mutation other than the hp-1 or the hp-1$^w$ mutation by either genotypic or phenotypic selection means, and detecting the presence of the hp-1 or the hp-1$^w$ mutation by means of the method disclosed hereinabove. In one preferred embodiment of this aspect of the invention, the phenotypic selection means for determining the presence of the non-hp-1, non-hp-1$^w$ photomorphogenic mutation comprises germinating seeds obtained from the plant in which the presence of the mutations is being determined in a temperature controlled chamber, under a yellow plastic screen that is opaque to light having a wavelength less than 500 nm, and selecting non-etiolated seedlings.

The present invention is also directed to a method for preparing double-mutant lines of *Lycopersicon esculentum* having genotype hp-1/hp-1 p/p, wherein p represents any recessive photomorphogenic lycopene-enhancing mutation that is genetically unlinked to the hp-1 mutation, said method comprising the steps of:
a) cross-hybridization of a homozygous hp-1/hp-1 line or plant with a homozygous p/p line or plant to yield double heterozygous hp-1/+ p/+ F$_1$ plants;
b) self-crossing of the F$_1$ plants obtained in step (a) in order to yield F$_2$ seeds;
c) identification of double homozygous plants hp-1/hp-1 p/p by means of the application of the method defined in claim 7 and a method for detecting the presence of the p mutation;
d) self-crossing of the double homozygous plants identified in step (c) to generate F$_3$ seeds, and germination of said seeds.

In one preferred embodiment of this aspect of the invention, the mutation p is the dg mutation. In this case, the determination of the presence of the dg mutation in step (c) of the method may be performed using the marker for the dg mutation disclosed in co-owned, co-pending application PCT/IL03/00023.

Similarly, the present invention is also directed to a method for preparing double-mutant lines of *Lycopersicon esculentum* having genotype hp-1$^w$/hp-1$^w$ p/p, wherein p represents any recessive photomorphogenic lycopene-enhancing mutation that is genetically unlinked to the hp-1$^w$ mutation, said method comprising the steps of:
a) cross-hybridization of a homozygous hp-1$^w$/hp-1$^w$ line or plant with a homozygous p/p line or plant to yield double heterozygous hp-1$^w$/+p/+F$_1$ plants;
b) self-crossing of the F$_1$ plants obtained in step (a) in order to yield F$_2$ seeds;
c) identification of double homozygous plants hp-1$^w$/hp-1$^w$ p/p by means of the application of the method defined in claim 10 and a method for detecting the presence of the p mutation;
d) self-crossing of the double homozygous plants identified in step (c) to generate F$_3$ seeds, and germination of said seeds.

In one preferred embodiment of this aspect of the invention, the mutation p is the dg mutation. In this case, the determination of the presence of the dg mutation in step (c) of the method may be performed using the marker for the dg mutation disclosed in co-owned, co-pending application PCT/IL03/00023.

The present invention also encompasses within its scope double-mutant hybrid plants of the species *Lycopersicon esculentum* having genotype hp-1/hp-1 p/p and (independently) hp-1$^w$/hp-1$^w$ p/p prepared by the above-disclosed methods.

All the above and other characteristics and advantages of the present invention will be further understood from the following illustrative and non-limitative examples of preferred embodiments thereof.

BRIEF DESCRIPTION OF THE DRAWINGS

FIG. 1. Nucleotide sequence of the genomic fragment (SEQ ID NO:19) used to design pyrosequencing primers for the hp-mutation (the single nucleotide polymorphism is in underlined large bold letters, the forward and the reverse primers are underlined and the sequencing primer is in italic).

FIG. 3. Typical pyrosequencing genotyping results for the hp-1 mutation at the DDB1 locus (Because of the reverse orientation of the sequencing primer, the mutant genotype is characterized by A and the normal genotype by T).

FIG. 5A and 5B. Complete nucleotide coding sequence of the normal wild-type tomato DDB1 gene (SEQ ID NO:36; the start, ATG, and the termination, TAG, codons are underlined. Location of $A^{931}$ and $G^{2392}$, whose transversion and transition leads to the hp-1 and hp-$1^w$ phenotypes 1 respectively, are in large bold letters), where the nucleotide sequence shown in FIG. 5A continues through 5B.

FIG. 6. Complete amino-acids sequence of the normal wild-type tomato DDB1 gene (SEQ ID NO: 37. Asparagine$^{311}$ and Glutamic-acid$^{798}$ whose substitution leads to the hp-1 and hp-$1^w$ phenotypes, respectively, are in large bold letters).

DETAILED DESCRIPTION OF PREFERRED EMBODIMENTS

Figure 2:
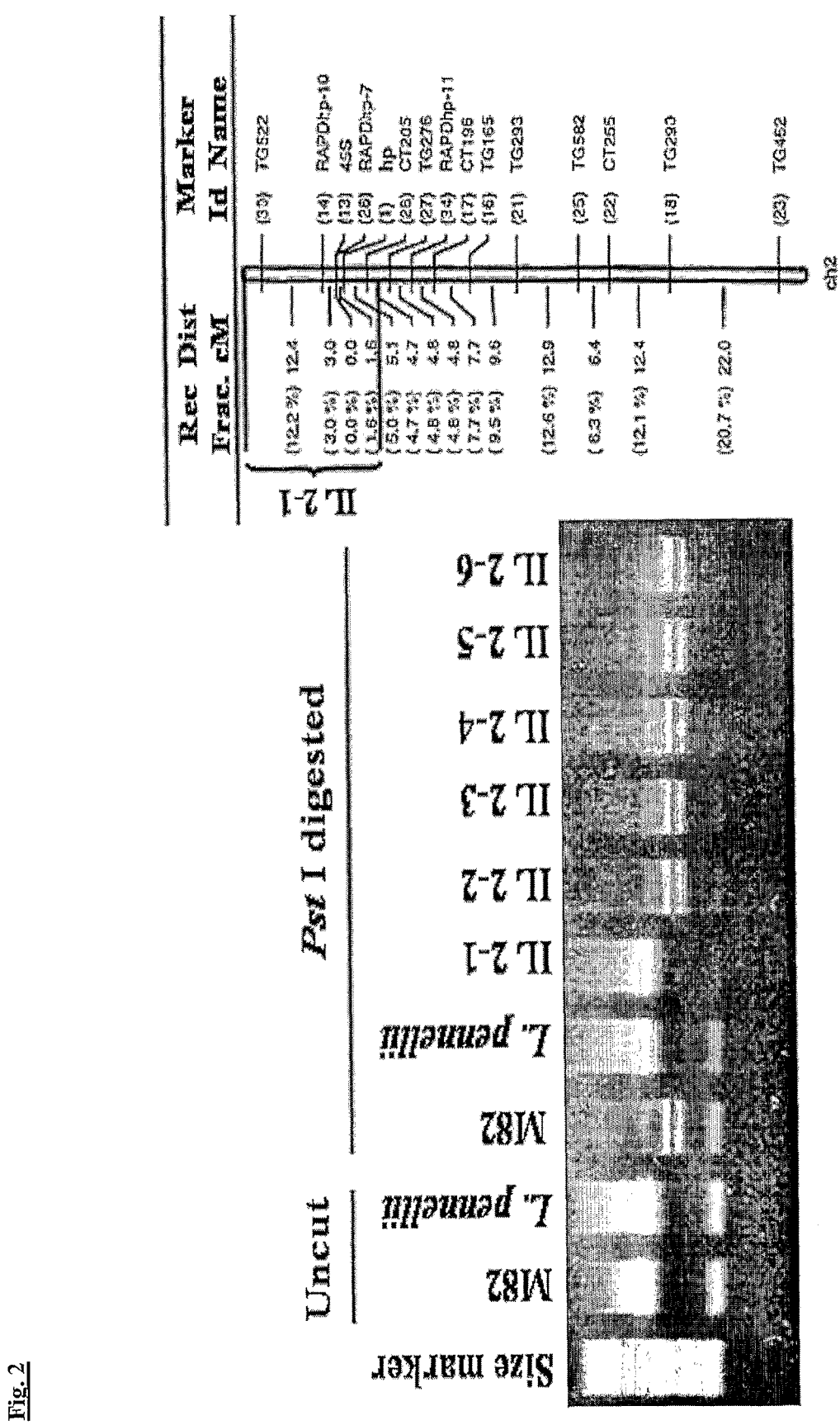
FIG. 2. Partial mapping results of the tomato DDB1 gene (map of the tomato chromosome 2, showing the location of the HP-1 gene (hp) was adopted from Yen et al. (1997)).

In one of its aspects, as described hereinabove, the present invention provides a method for detecting the presence of the hp-1 and hp-$1^w$ mutations in a plant.

In the case of the hp-1 mutation, this method comprises the steps of isolating a genomic DNA fragment comprising the region of the DDB1 gene containing the site of the single nucleotide polymorphism (SNP) responsible for the hp-1 phenotype (at nucleotide position 931), cloning said fragment, sequencing said cloned fragment and determining the presence of the hp-1 mutation by means of detecting the A/T transversion at position 931 of the sequenced genomic fragment.

In a particularly preferred embodiment of this method of the present invention, the sequencing of the cloned fragment is achieved by means of a pyrosequencing reaction. Prior to the pyrosequencing reaction, the SNP-containing genomic fragment is amplified by means of a PCR technique, the details of which will be described hereinbelow.

The term "PCR" (or polymerase chain reaction) technique as used hereinabove and hereinbelow refers to a family of techniques that are based on the use of heat-stable polymerases for achieving the amplification (i.e. increase in number of copies) of specific DNA sequences by repeated polymerase reactions. This reaction can be used as a replacement for cloning: all that is required is knowledge of the nucleic acid sequence. In order to carry out PCR, primers are designed which are complementary to the sequence of interest. The primers are then generated by automated DNA synthesis.

PCR and other methods of amplifying DNA and/or RNA are well known in the art, and can be used according to the present invention without the need for undue experimentation, based on the teaching and guidance presented herein. Several PCR methods (as well as related techniques) are described, for example, in U.S. Pat. Nos. 4,683,195, 4,683, 202, 4,800,159, 4,965,188, as well as in Innis et al. eds., *PCR Protocols: A guide to method and applications.*

The following examples are provided for illustrative purposes and in order to more particularly explain and describe the present invention. The present invention, however, is not limited to the particular embodiments disclosed in these examples.

EXAMPLES

Materials and Methods

Plant Material and Crosses

Seeds from the normal, open pollinated, tomato (*Lycopersicon esculentum*) cv. Ailsa Craig and a line nearly isogenic and homozygous for the hp-1 mutation were kindly provided by J. J. Giovannoni, of the Boyce Thompson Institute for Plant Research, Ithaca, N.Y., USA.

Seeds from cv. Rutgers homozygous for the a hp-1 mutation (LA3004), as well as seeds from hp-$1^w$/hp-$1^w$ mutant plants and their isogenic normal plants in GT background (LA LA4012 and LA4011, respectively), were provided by R. T. Chetelat, of the Tomato Genetics Cooperative, UC Davis, Calif., USA. The genotype GT is a tomato breeding line, resistant to mosaic virus, and similar in morphology to cv. Moneymaker, originally obtained from Deruiterzonen, Bleiswijk, the Netherlands (Koornneef et al. 1990). The hp-$1^w$/hp-$1^w$ mutant plants appeared among progeny of a plant raised from EMS-treated seeds of the genotype GT (Peters et al. 1989). Therefore, these plants are highly isogenic to the normal GT genotype. Mutant hp-$1^w$/hp-$1^w$ plants show a more extreme phenotype compared to hp-1/hp-1 plants, and it was clearly shown that hp-1 and hp-$1^w$ are allelic (Peters et al. 1989).

A processing hp-1/hp-1 mutant hybrid, LRT89, two hp-1/hp-1 breeding lines, L525 and L527, and a normal breeding line, N671, were developed by the late R. Frankel, D. Lapushner and I. Levin at the Volcani Center. Seeds from two hp-1/hp-1 processing hybrids, HA3501 and HA3502, developed by Hazera Genetics Inc., Israel, were provided by Mr. Ezri Peleg. Seeds of the heterozygous hp-1/+ cultivar, cv. 124, were also provided by Hazera Genetics Inc., Israel. Several normal +/+ tomato cultivars used in this study, i.e.: Moneymaker, M82, Brigade, VF-36, 189, Manapal, NC8288 and Florida, were from seed stocks available at the Volcani center. DNA was also extracted from single plants of AB427, AB510 and AB747, three hp-1/hp-1 processing hybrids developed by AB Seeds Inc., Israel.

Normal cv. Ailsa Craig plants were crossed with their nearly isogenic hp-1 mutant plants to yield $F_1$ seeds. These $F_1$ plants were allowed to self pollinate to yield $F_2$ seeds. A sample of 123 $F_2$ seedlings was used for the linkage analysis carried out in this study.

Genomic DNA Extraction and Southern Blot Hybridization

Genomic DNA was extracted from individual plants according to Fulton et al. 1995. To determine the copy number of the DDB1 gene in the tomato genome, Southern blot hybridization was carried out according to the following procedure: Genomic DNA extracted from both *L. esculentum* (cv. M82) and *L. pennellii* was digested with EcoR I, EcoR V, Dra I, Hae III, Sca I, and Mva I restriction endonucleases. Following electrophoresis in 1.0% agarose gel and Southern transfer, the DNA was hybridized with a $P^{32}$ labeled DNA probe containing 1346 bp of the 5' coding sequence of the DDB1 gene. Southern blot transfer and DNA hybridization were done according to Levin and Smith (1990).

Design of PCR Primers

Sequence analysis and locus-specific primer design were carried out with the DNAMAN, Sequence Analysis Software version 4.1 (Lynnon BioSoft, Quebec, Canada). All DNA primers used were purchased from M.B.C Molecular Biology Center Ltd., Ness-Ziona, Israel.

PCR Reactions

PCR reactions were used for mapping, cloning and amplification of DNA products for direct sequencing and pyrosequencing. For all of these purposes, the amplification reactions (25 ml final volume) were performed with 10 ng template DNA, 25 mM TAPS (pH=9.3 at 25° C.), 50 mM KCl, 2 mM MgCl2, 1 mM B-mercaptoethanol, 0.2 mM of each of the four deoxyribonucleotide triphosphates (dATP, dCTP, dGTP and dTTP), 10 pmoles of each of two primers and 1 unit of thermostable Taq DNA polymerase (SuperNova Taq polymerase, Madi Ltd., Rishon Le Zion, Israel). Reactions were carried out in an automated thermocycler (MJ Research Inc., Watertown, Mass., USA).

For mapping and direct sequencing, initial incubation was at 94° C. for 3 min, followed by 35 cycles of denaturation at 94° C. for 30 sec, annealing at 58° C. for 30 sec, and polymerization at 72° C. for 1-2 min, depending upon the PCR product size. Final polymerization at 72° C. was carried out, for 5 min, after completion of the above cycles. The PCR amplification products were visualized by electrophoresis in 1.0% agarose gels and detected by staining with ethidium bromide.

For the PCR amplification preceding the pyrosequencing reaction, initial incubation was at 94° C. for 2 min, followed by 35 cycles of denaturation at 94° C. for 30 sec, annealing at 57° C. for 30 sec, and polymerization at 72° C. for 20 sec. Final polymerization at 72° C. was carried out, for 5 min, after completion of the above cycles.

Mapping the DDB1 Gene

DDB1 was mapped by means of *Lycopersicon* (L.) *pennellii* introgression lines (Eshed et al. 1992). DNA extracted from individual plants of each of the introgression lines, including their original parental lines M82 and *L. pennellii*, were used as templates in PCR reactions. The primers used for these mapping reactions were mTDDB F and mTDDB R (Table 1). These primers were derived from the Institute of Genomic Research (TIGR) database accession TC117372 (http://www.tigr.org/) that was found highly homologous to both copies of the *A. thaliana* DDB1 gene. To obtain polymorphism between M82 and *L. pennellii*, the PCR products were digested with Pst I endonuclease, following the PCR reaction.

Cloning and Sequencing of the Tomato DDB1 cDNA from hp-1 and hp-1$^w$ Mutant Plants Total RNA was extracted from 25 mg of leaf tissue of individual hp-1 and hp-1$^w$ mutant seedlings and their nearly isogenic open pollinated wild-type genotypes (Ailsa Craig and GT, respectively). The RNA extraction was carried out using the TRIzol reagent system (GibcoBRL Life Technologies, Gaithersburg, Md., USA). Total RNA was used as the template for first-strand cDNA synthesis using the Superscript pre-amplification system (GibcoBRL Life Technologies, Paisley, UK). The cDNA prepared was used as a template in PCR reactions, to amplify overlapping fragments of the gene encoding the tomato DDB1, from in both mutant and normal genetic accessions. The PCR products were then sequenced, either directly or after cloning into pGEM-T Easy Vector using the pGEM-T Easy Vector Systems, according to the manufacturer recommendations (Promega, Madison, Wis., USA). After cloning into pGEM-T Easy Vector, four or five independent clones of each of the overlapping amplified fragments were sequenced, based on the vector T7, SP6, and primers complementary to the tomato DDB1 gene. Whenever direct sequencing was used, at least two PCR products, representing each primer combination complementary to the tomato DDB1 gene, were sequenced. Sequencing was carried out with an ABI PRISM 377 automated DNA sequencer (Applied Biosystems, Foster City, Calif., USA).

The 3' region of the tomato DDB1 gene was directly sequenced by using overlapping fragments amplified with primers complementary to TIGR data base accession TC117372 (http://www.tigr.org/) that is highly homologous to both copies of the *A. thaliana* DDB1 gene. These primers are presented in Table 1, below:

TABLE 1

Forward (F) and reverse (R) primers, complementary to TIGR database accession TC117372, used to sequence the 3' region of the tomato DDB1 gene.

| Primer name | Primer sequence | Sequence list ref. no. |
|---|---|---|
| 5TDDE F | 5'-ACGACCTATCGTGGACTTCTGT-3' | SEQ ID NO: 3 |
| 5TDDB R | 5'-CTGGACTTGAGAATTGAAGCCT-3' | SEQ ID NO: 4 |
| In5TDDB F | 5'-GAGCCTATAAGGATGGATCAC-3' | SEQ ID NO: 5 |
| ATDDB F | 5'-CAGCAGTTGGAATGTGGACAG-3' | SEQ ID NO: 6 |
| mTDDB F | 5'-GCAATCGCTAAAGAAGGTGAGT-3' | SEQ ID NO: 7 |
| mTDDB R | 5'-GCATTATAGTCTCTGGCTCGCT-3' | SEQ ID NO: 8 |
| inmTDDB F | 5'-GGACATTTGCTCTATGCAGT-3' | SEQ ID NO: 9 |
| inmTDDB R | 5'-AGGCATTTAGAGAGTAGACAGC-3' | SEQ ID NO: 10 |
| TDDB F | 5'-TTTGGAGAAGCTGCAGAGAA-3' | SEQ ID NO: 11 |
| TDDB R | 5'-CACAACCTCACAGAAGAAGAAG-3' | SEQ ID NO: 12 |
| In3TDDB R | 5'-CCACTCTCTTCATTAGTTCCTC-3' | SEQ ID NO: 13 |

The 5' region of the DDB1 gene was initially cloned from a pBluescript® SK(+/−) phagemid cDNA library with the following primers:

```
                                            (SEQ ID NO: 14)
T7 = 5'-GTAATACGACTCACTATAGGGC-3'
and

5'TDDB_R = 5'-CTGGACTTGAGAATTGAAGCCT-3'
```

This cDNA library, kindly provided by R. Barg and Y. Salts, of the Volcani Center, Israel, was prepared from young parthenocarpic fruits of 4-6 mm in diameter (ca. 4-8 days post-anthesis) derived from the facultative parthenocarpic determinate line L-179 (pat-2/pat-2). This line was described previously (Barg et al. 1990). The library was prepared with the cDNA Synthesis Kit#200400, Zap-cDNA Synthesis Kit#200401, and Zap cDNA Gigapack III Gold Cloning Kit#200450 of Stratagen Inc., according to the of the manufacturer's instructions.

The 5' region of the tomato DDB1 gene from hp1/hp1 and hp1$^w$/hp1$^w$ mutant lines and their corresponding nearly isogenic normal lines was directly sequenced using the above primer (5'TDDB_R) and the primer TDB_UTR=5'-AT-AGCGGGAAGAGGGAAGATAC-3' (SEQ ID NO:15), that is complementary to the 5' UTR of the tomato DDB1 gene. Several overlapping primers complementary to the above fragment, such as those used for pyrosequencing genotyping (see below), were used for sequence verification of the 5' coding sequence of the tomato DDB1 gene.

Linkage Analysis

The analysis of linkage between the tomato DDB1 locus and the exaggerated photomorphogenic de-etiolation response characterizing hp-1 mutant, was carried out using $F_2$ seeds of a cross between hp-1 mutant plants and wild-type plants (cv. Ailsa Craig). These seeds were allowed to germinate under a yellow plastic screen that prevented the transmission of light of wavelengths under 500 nm (Mochizuki and Kamimura 1984), in an environmentally controlled growth chamber (25° C. day/18° C. night). These germination and initial growth conditions result in exaggeration of hypocotyl-length differences between the mutant and normal plants (Mochizuki and Kamimura, 1984). The hypocotyl lengths of individual $F_2$ seedlings were measured 8 days after sowing, and their genotype was determined with the pyrosequencing-based DNA marker disclosed and described herein.

Pyrosequencing Genotyping

A pyrosequencing genotyping system (extensively reviewed by Ronaghi 2001) based on the above-described single nucleotide polymorphism (SNP) between hp1/hp1 mutant line and its nearly isogenic normal line in cv. Ailsa Craig background was developed. For this purpose a genomic fragment containing the SNP was cloned and sequenced as presented in FIG. 1. The biotin-labeled forward primer for this reaction was 5'-TGTTTTCCAGAGTTACCGGACT-3' (SEQ ID NO:16); the reverse primer was 5'-TAGCTTGAGC-CAATGAAGACAA-3' (SEQ ID NO:17); and the sequencing primer was 5'-ATGAAGACAAAAGCAT-3' (SEQ ID NO:18). The amplicon size in this reaction was 106 bp.

The PCR amplification reaction preceding the pyrosequencing reaction was as described above (see PCR reactions). Two pmoles of the sequencing primer were added to the amplification reaction prior to the pyrosequencing analysis. The analysis was carried out using a MegaBASE 1000 instrument (Danyel Biotech, Nes Ziona, Israel). Because the sequencing primer is in reverse orientation, the normal genotype is characterized by T whereas the homozygous mutant hp-1 genotype is characterized by A at the SNP location, as shown in FIG. 3.

Statistical Analyses

Analyses of variance (ANOVA) were carried out with the JMP Statistical Discovery software (SAS Institute, Cary, N.C., USA). Linkage analysis and LOD score determination were carried out with the QGENE software Version 3.06d (Nelson 1997). Alignment of amino-acid sequences was carried out using the Clustal method (Higgins and Sharp 1988).

Example 1

Identification and Cloning of the Tomato Homolog of DDB1

The DDB1 protein is a heterodimer consisting of two subunits, DDB1 and DDB2. Unlike rice, chicken, human, mouse, Drosophila and Schizosaccharomyces pombe, the A. thaliana genome harbors two highly homologous copies of the DDB1 gene (Schroeder et al. 2002; Zolezzi et al. 2002; Fu et al. 2003; Ishibashi et al. 2003): DDB1A, and DDB1B, both 1088 amino-acids in length (Genbank protein accessions NP_192451 and NP_193842, respectively). When each of these two protein accessions were used as a query in tblastn analysis against the TIGR database (http://www.tigr.org/) containing tomato Expressed Sequence Tags (EST), both revealed two highly homologous sequences: TC117371 (394 bp) and TC117372 (2206 bp). The A. thaliana Accession NP_192451 was found to share 87 and 86% identities with the tomato TC117371 and TC117372 accessions, respectively. Accession NP_193842, on the other hand, shared 87 and 83% identities with the tomato TC117371 and TC117372 accessions, respectively. Careful sequence analysis, based initially on the longer TIGR accession, TC117372, and later on the single gene that we had cloned from a cDNA library, made it clear to us that the two tomato TIGR accessions, TC117371 and TC117372, were complementary to the same gene sequence. Moreover, Southern-blot transfer and hybridization of tomato genomic DNA, with the DDB1 gene sequence as a probe, revealed that indeed the tomato genome contains a single copy of the DDB1 gene (data not presented).

Example 2

Mapping of the Tomato DDB1

Partial mapping results, that include the approximate map location of the tomato DDB1 gene, are presented in FIG. 2. These results indicate that the DDB1 is located on the tomato chromosome 2, in the introgression line that harbors the HP-1 gene (Yen et al. 1997).

Example 3

Sequence Characterization of the Tomato DDB1 in hp-1 and hp-1$^w$ Mutants

Figure 4:
FIG. 4. Partial ClustalW protein Alignment of DDB1 showing the location of the hp-1 (a) and hp-1$^w$ (b) amino-acid substitutions for *Arabidopsis* DDB1A (hp-1 SEQ ID NO:20; hp-1$^w$ SEQ ID NO:21) (At_DDB1A=NP_192451), *Arabidopsis* DDB1B (hp-1 SEQ ID NO:22; hp-1$^w$ SEQ ID NO:23) (At_DDB1B=NP_193842), tomato cv. Ailsa Craig (hp-1 SEQ ID NO:24; hp-1$^w$ SEQ ID NO:25) (Le=AY452480), rice (hp-1 SEQ ID NO:26; hp-1$^w$ SEQ ID NO:27) (Os=BAB20761), human (hp-1 SEQ ID NO:28; hp-1$^w$ SEQ ID NO:29) (Hs=DDB1_Human), *Drosophila* (hp-1 SEQ ID NO:30; hp-1$^w$ SEQ ID NO:31) (Dm=XP_081186), chicken (hp-1 SEQ ID NO:32; hp-1$^w$ SEQ ID NO:33) (Gg=BAC56999), and *S. pombe* (hp-1 SEQ ID NO:34; hp-1$^w$ SEQ ID NO:35) (Sp=NP_593580). Identical residues are black shaded whereas similar residues are gray shaded.

Several forward and reverse primers (Table 1), complementary to the 3' region of the tomato DDB1 gene (TIGR accession TC117372), were used in order to perform direct sequencing on cDNA prepared from leaves of seedlings from hp-1 and normal plants in Ailsa Craig background. No polymorphism was obtained between hp-1 and normal plants in this region. The 5' region of the DDB1 gene in the two genotypes was therefore cloned and thoroughly sequenced as well. Computerized translation of all sequence results showed that the tomato DDB1 is a 1090-amino-acid protein. Sequence analysis of the DDB1 coding sequence from hp-1 and its nearly isogenic normal genotype revealed a single $A^{931}$-to-$T^{931}$ base transversion in the coding sequence of DDB1 gene of the mutant hp-1 plants. This transversion resulted in a substitution of a conserved Asparagine$^{311}$ to Tyrosine$^{311}$ (FIG. 4).

Based on the sequence information obtained in the Ailsa Craig background, we have also sequenced the entire coding region of the DDB1 gene in hp-1$^w$ mutant plant and its isogenic normal counterpart in GT background. Because hp-1$^w$ is allelic to hp-1, a major mutation in the coding sequence of the DDB1 gene in hp-1$^w$ mutants would strongly support the hypothesis that the tomato DDB1 gene causes both the hp-1 and hp-1$^w$ mutant phenotypes. Indeed, a single $G^{2392}$-to-$A^{2392}$ transition was observed in the DDB1 coding sequence in the hp-1$^w$ mutant plant which results in a substitution of a conserved Glutamic-acid$^{798}$ to Lysine$^{798}$ (FIG. 4).

The complete nucleotide coding sequence and the deduced amino acids sequence of the normal wild-type tomato DDB1 gene are shown in FIG. 5 and FIG. 6, respectively.

Example 4

Genotyping of Lines and Cultivars

Nineteen lines or cultivars, obtained from various sources, were genotyped by a combination of direct sequencing and pyrosequencing methods (FIG. 3). Included among them were a single heterozygous hp-1/+, 10 hp-1/hp-1 and eight normal +/+ accessions. Complete agreement between the SNP identified at the DDB1 gene and the known genotype of the plants at the HP-1 locus was found (results not shown).

Example 5

Analysis of the Linkage Between the DDB1 Locus and the Photomorphogenic Response A linkage analysis study was carried out to test the association between the DDB1 locus and the characteristic hypersensitive-photomorphogenic response displayed by hp-1 mutant seedlings (i.e., the inhibition of hypocotyl elongation phenotype). For this purpose, $F_2$ seeds of a cross between determinate hp-1 mutant plants and wild type plants (cv. Ailsa Craig) were germinated under yellow plastic screen in a controlled growth chamber. Eight days after sowing, the hypocotyls lengths of individual seedlings were recorded, and their DDB1 locus was genotyped with aid of the pyrosequencing DNA marker, as described above. The results demonstrate a clear association between the DDB1 locus and hypocotyls length, as shown in Table 2, below:

TABLE 2

Linkage analysis between the tomato DDB1 locus and the photomorphogenic response displayed by hp-1 mutant seedlings.

| Genotype | N | Hypocotyl length ± S.E. (cm) | LOD score | $R^2$ |
|---|---|---|---|---|
| +/+ | 35 | $9.6^A \pm 0.2$ | 25 < LOD < 26 | 62.8% |
| hp-1/+ | 68 | $8.7^B \pm 0.2$ | | |
| hp-1/hp-1 | 20 | $4.2^C \pm 0.2$ | | |

Seedlings were grown under a yellow plastic screen for 8 days after sowing. Different superscript letters indicate statistically significant differences between means (P < 0.05) according to the Tukey-Kramer HSD test (Kramer 1956).

Homozygous recessive hp-1/hp-1 seedlings displayed a highly significant inhibition of hypocotyl elongation, indicative of a more exaggerated photomorphogenic de-etiolation response, in comparison to the two other two genotypic groups (25<LOD Score<26, $R^2$=62.8%). These results confirm that the mutation identified in the DDB1 locus of hp-1 mutant plants is associated with one of its main characteristic phenotypes, i.e., inhibited hypocotyl elongation in the seedlings. Interestingly, a slight partially dominant effect for the hp-1 allele was obtained in this study. This effect can be noted from the statistically significant differences obtained between the +/+ and hp-1/+ group means (Table 2).

Further non-limiting examples (both working and theoretical) that illustrate and describe various practical embodiments of the present invention are given in the following sections. These embodiments are described for illustrative purposes only, and are not intended to limit the scope of the present invention in any way.

Example 6

Diagnostic Tool for Identifying the hp-1 and hp-1$^w$ Mutations

A pyrosequencing DNA marker system, extensively reviewed by Ronaghi 2001, for use as a molecular diagnostic tool for identifying hp-1 mutant plants based on the sequence results (FIG. 1) was developed. This DNA marker is based on the single nucleotide polymorphism (SNP) discovered in this study between hp1/hp1 mutant line and its nearly isogenic normal line in cv. Ailsa Craig background. For this purpose a genomic fragment containing the SNP was cloned and sequenced. The sequence of this genomic fragment is presented in FIG. 1. The biotin labeled forward primer for this reaction was: 5'-TGTTTTCCAGAGTTACCGGACT-3' (SEQ ID NO:16); the reverse primer was: 5'-TAGCTTGAGCCAATGAAGACAA-3' (SEQ ID NO:17); and the sequencing primer was 5'-ATGAAGACAAAAGCAT-3' (SEQ ID NO:18). The amplicon size in this reaction was 106 bp.

The PCR amplification reaction preceding the pyrosequencing reaction was as described (see PCR reactions above). Two pmoles of the sequencing primer were added to the amplification reaction prior to the pyrosequencing analysis. The analysis was carried out using a MegaBASE 1000 instrument by Danyel Biotech, Nes Ziona, Israel. Because the sequencing primer is in reverse orientation, the normal genotype is characterized by T whereas the homozygous mutant hp-1 genotype is characterized by A at the SNP location as presented in FIG. 3.

Using the pyrosequencing methodology and the primers described above a clear polymorphism between hp-1 and wild-type plants was seen as demonstrated in FIG. 3. In the case of the homozygous hp-1 mutant plants, a single peak representing Adenine (A) at the SNP location was observed, while in wild-type plants, a single peak representing Thymine (T) at the SNP location was observed (FIG. 3). As expected, plants heterozygous for the hp-1 mutation yielded two peaks, representing both A an T nucleotides (FIG. 3).

A similar pyrosequencing based marker system based on the SNP observed in hp-1$^w$ mutant plants has also been established.

Example 7

Incorporation of Two Genetically Unlinked Lycopene Enhancing Mutations in a Single Tomato Hybrid: Experimental Approach A common practice among breeders is to combine or incorporate two or more mutations positively affecting the same trait. Such procedure can be verified by laborious and time consuming test crosses. The diagnostic tool produced herein can facilitate the incorporation of two light hypersensitive lycopene-enhancing mutations in a single plant or breeding line.

Several mutations in tomato positively affect lycopene content in the mature tomato fruit. Of these, at least 5 show a significant hypersensitive light response. These include:
1. High pigment-1 (hp-1)
2. High pigment-1$^w$ (hp-1$^w$)
3. High pigment-2 (hp-2)
4. High pigment-2$^j$ (hp-2$^j$)
5. Dark green (dg)

The hp-1 and hp-1$^w$ mutations map to the HP-1 locus on the tomato chromosome 2 (Yen et al. 1997 and in accordance with the present invention). The hp-2, hp-2$^j$ and dg mutations map to the HP-2 locus on the tomato chromosome 1 (Mustilli et al. 1999; Levin et al. 2003). Incorporation of lycopene enhancing hp-2, hp-2$^j$ or dg at the HP-2 locus and either one of the two mutations that map to the HP-1 locus (hp-1 and hp-1$^w$) can be more efficiently achieved through the following procedure (illustrated for the dg and hp-1 mutations):
1. Cross homozygous dg with homozygous hp-1 mutants to generate double heterozygous $F_1$ plants:

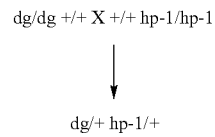

2. Self-cross the $F_1$ double heterozygous plants to generate $F_2$ seeds. These $F_2$ seeds will segregate into 9 genotypes: dg/dg hp-1/hp-1, dg/dg hp-1/+, dg/dg +/+, dg/+ hp-1/hp-1, dg/+ hp-1/+, dg/+ +/+, +/+ hp-1/hp-1, +/+ hp-1/+, +/+ +/+.

Using the pyrosequencing marker system for the hp-1 mutation disclosed herein and the marker for the dg mutation disclosed in co-owned pending application PCT/IL03/00023, the double homozygous plants dg/dg hp-1/hp-1 can be easily identified and self-crossed to yield a breeding line homozygous for the two mutations.

Example 8

Incorporation of Two Genetically Unlinked Lycopene Enhancing Mutations in a Single Tomato Hybrid Significantly Increases Lycopene Yield: Working Example Two semi-isogenic hybrids, one homozygous for the hp-1 mutation, hp-1/hp-1, and the other for the dg mutation, dg/dg, were crossed hybridized to yield $F_1$ plants (hp-1/+dg/+). These $F_1$ plants were self-hybridized to yield $F_2$ seedlings. These $F_2$ seedlings were genotyped and self-hybridized to yield double mutant plants (hp-1/hp-1 dg/dg), as outlined in Example 7. Two horticulturally acceptable plants were selected and allowed to self hybridize to yield two $F_4$ lines. These $F_4$ lines were cross hybridized to yield a double mutant hybrid. This hybrid was tested, together with the semi-isogenic single mutant hybrids used in the initial cross (see above), in 4 locations in northern Israel during the spring season under open field conditions. Results presented in Table 3 (below) show that, unexpectedly, the lycopene yield of the double mutant hybrid is statistically higher compared to its isogenic single mutant hybrids. The increase in lycopene yield of the double mutant hybrid was 19 and 61% compared to the lycopene yield of the dg/dg and hp-1/hp-1 single mutant hybrids, respectively.

TABLE 3

Lycopene yield of single and double mutant hybrid cultivars carrying hypersensitive lycopene-enhancing mutations.

| Cultivar genotype | Lycopene yield (gr/dunam*) |
|---|---|
| +/+ hp-1/hp-1 | $1136^C$ |
| dg/dg +/+ | $1538^B$ |
| dg/dg hp-1/hp-1 | $1824^A$ |

Different superscript letters represent statistically significant differences between means (P < 0.05) based on Tukey-Kramer HSD test (Kramer, 1956).
*1 dunam = 1000 square meters Example 9

Use of the Diagnostic Tool for Post Control Analysis of Parental Lines and Hybrid Seeds Seed companies often use a battery of molecular markers for post- or quality-control of parental seed stocks and hybrid-seeds. Several commercial lycopene-rich tomato cultivars carry the hp-1 and hp-$1^w$ mutation either at a homozygous or heterozygous state. Up until now, detection of the hp-1 and hp-$1^w$ traits within a particular stock could only be performed by the lengthy procedure of germinating samples of the seeds, and performing complicated phenotypic analyses on the parental cultivars and subsequent generations.

The diagnostic tool demonstrated in this study (see Example 6, hereinabove) can be used to positively detect the hp-1 and hp-$1^w$ alleles in such cultivars and their parental lines, and thus enable post-production quality control to be carried out over a time scale of 1-2 days instead of weeks or months.

Example 10

Mapping of Other Functionally Active Mutations in the DDB1 Gene

Seeds extracted from normal plants can be mutagenized with ethyl methanesulfonate (EMS) or other approaches according to known protocols to yield photomorphogenic mutants (Koornneef et al. 1990). These mutants can be selected for under modulated light conditions, such as yellow plastic screen. Photomorphogenic mutants obtained can be screened for unique expression patterns of health-promoting metabolites. These mutants can be further characterized by allele tests against hp-1 and/or hp-$1^w$ and some of them may be characterized as allelic to these mutations. Thus, mutagenized plants allelic to hp-1 and/or hp-$1^w$ can be discovered that also bear unique metabolite profiles. Sequence analysis of the DDB1 gene in these plants should reveal the exact genetic modifications that underline such unique metabolic architectures. These genetic modifications should enable the design of specific molecular markers, similar to those outlined hereinabove, for marker assisted selection. Also, mapping of such lesions may unravel regions within the DDB1 gene as targets for efficient genetic manipulation to obtain plants with unique metabolite profiles in the tomato fruit.

Example 11

Over-Expression of Normal or Modified DDB1 Genes to Obtain Over-Production of Health Promoting Metabolites in the Tomato Fruit and/or Fruits and Vegetables of Other Plant Species The DDB1 gene is highly conserved across many evolutionary distant species (Schroeder et al. 2002). Also, its link to overproduction of heath-promoting metabolites has been outlined hereinabove. These results suggest that effects of the DDB1 gene on the production of health promoting compounds should not be ignored in other plant species as well. From such practical point of view, the DDB1 gene may be cloned from normal or hp-1 and hp-$1^w$ mutant tomato plants, or any other plant species, in sense or anti-sense (RNAi) orientations under constitutive or fruit-specific promoters. Over-expression of any of these constructs in any plant species may result in increases in the production of functional metabolites in fruits and vegetables.

REFERENCES

Barg R, Meir E, Lapushner D, Frankel R, Salts Y (1990) Differential regulation of fruit specific 62 kDa protein in developing parthenocarpic (pat-2/pat-2) and seeded tomato fruits. *Physiol Plant* 80:417-424

Chory J (1993) Out of darkness: mutants reveal pathways controlling light-regulated development in plants. Trends Genet 9:167-172

Eshed Y, Abu-Abied M, Saranga Y, Zamir D (1992) Lycopersicon esculentum lines containing small overlapping introgressions from *L. pennellii*. Theor Appl Genet 83:1027-1034

Fu D, Wakasugi M, Ishigaki Y, Nikaido O, Matsunaga T (2003) cDNA cloning of the chicken DDB1 gene encoding the p127 subunit of damaged DNA-binding protein. Genes Genet Syst 2003 78:169-77

Fulton T M, Chunwongse J, Tansley S D (1995) Microprep protocol for extraction of DNA from tomato and other herbaceous plants. Plant Mol Biol Rep 13:207-209

Higgins D G, Sharp P M (1988) CLUSTAL: a package for performing multiple sequence alignment on a microcomputer. Gene 73:237-244.

Ishibashi T, Kimura S, Yamamoto T, Furukawa T, Takata K, Uchiyama Y, Hashimoto J, Sakaguchi K (2003) Rice UV-damaged DNA binding protein homologues are most abundant in proliferating tissues. Gene 308:79-87

Konsler T R (1973) Three mutants appearing in 'Manapal' tomato. HortSci 8:331-333

Koornneef M, Bosma T D G, Hanhart C J, van der Veen J H, Zeevaart J A D (1990) The isolation and characterization of gibberellin-deficient mutant in tomato. Theor Appl Genet 80:852-857

Kramer C Y (1956) Extension of multiple range tests to group means with unequal number of replications. Biometrics 12:309-310

Levin I, Frankel P, Gilboa N, Tanny S, Lalazar A (2003) The tomato dark green mutation is a novel allele of the tomato homolog of the DEETIOLATED1 gene. Theor Appl Genet 106:454-460

Levin I, Smith E J (1990) Molecular analysis of endogenous virus ev21-slow feathering complex of chickens. 1. Cloning of proviral-cell junction fragment and unoccupied integration site. Poult Sci 69:2017-2026

Mochizuki T, Kamimura S (1984) Inheritance of vitamin C content and its relation to other characters in crosses between hp and og varieties of tomatoes. Eucarpia Tomato Working Group. Synopsis IX meeting 22-24 May, Wageningen, the Netherlands, pp 8-13

Mustilli A C, Fenzi F, Ciliento R, Alfano F Bowler C (1999) Phenotype of the tomato high pigment-2 is caused by a mutation in the tomato homolog of DEETIOLATED1. Plant Cell 11:145-157

Nelson J C (1997) QGENE: software for marker-based genomic analysis and breeding. Mol Breed 3:229.235

Peters J L, van Tuinen A, Adamse P, Kendrick R E, Koornneef M (1989) High pigment mutants of tomato exhibit high sensitivity for phytochrome action. J Plant Physiol 134: 661-666

Reynard G B (1956) Origin of Webb Special (Black Queen) in tomato. Rep Tomato Genet Coop 40: 44-64

Ronaghi M (2001) Pyrosequencing sheds light on DNA sequencing. Genome Res 11:3-11

Schroeder D F, Gahrtz M, Maxwell B B, Cook R K, Kan J M, Alonso J M, Ecker J R, Chory J (2002) De-etiolated 1 and damaged DNA binding protein 1 interact to regulate *Arabidopsis* photomorphogenesis. Curr Biol. 12:1462-1472

Soressi G P (1975) New spontaneous or chemically-induced fruit ripening tomato mutants. Rep. Tomato Genet Coop 25:21-22 van Tuinen A, Cordonnier-Prat M-M, Pratt L H, Verkerk R, Zabel P, Koornneef M (1997). The mapping of phytochrome genes and photomorphogenic mutants of tomato. Theor Appl Genet 94:115-122

Wann E V, Jourdain E L, Pressey R Lyon B G (1985) Effect of mutant genotypes hp $og^c$ and dg $og^c$ on tomato fruit quality. J Amer Soc Hort Sci 110:212-215

Yen H, Shelton A, Howard L, Vrebalov J, Giovanonni J J (1997) The tomato high-pigment (hp) locus maps to chromosome 2 and influences plastome copy number and fruit quality. Theor Appl Genet 95:1069-1079

Zolezzi F, Fuss J, Uzawa S, Linn S (2002) Characterization of a *Schizosaccharomyces pombe* strain deleted for a sequence homologue of the human damaged DNA binding 1 (DDB1) gene. J Biol Chem 277:41183-411891

The invention claimed is:

1. An isolated nucleotide sequence responsible for the tomato high pigment 1 (hp-1) phenotype, wherein said sequence comprises sequence SEQ ID NO: 1.

2. A method for detecting the presence of the hp-1 mutation in a plant, said method comprising the steps of:
   (i) isolating the genomic DNA from said plant, amplifying a gene fragment containing the hp-1 mutation represented by T at nucleotide position 212 of SEQ ID NO: 19 from the genomic DNA by use of a PCR technique; and
   (ii) determining the presence of the hp-1 mutation in the genomic DNA.

3. The method of claim 2, wherein the gene fragment comprises nucleotides 135 to 240 of SEQ ID NO: 19.

4. The method according to claim 2, wherein the presence of the hp-1 mutation is determined by the use of a pyrosequencing technique, and wherein the sequence data obtained from said technique is compared with the sequence defined in SEQ ID NO: 1.

5. The method according to claim 2, wherein the plant in which the presence of the hp-1 mutant is being detected is of the species *Lycopersicon esculentum*.

* * * * *